(12) United States Patent
Maresh et al.

(10) Patent No.: US 8,386,278 B2
(45) Date of Patent: *Feb. 26, 2013

(54) METHODS, SYSTEMS, AND DEVICES FOR MANAGING TRANSFER OF MEDICAL FILES

(75) Inventors: Guy Maresh, Sherwood, OR (US); Jeffrey N. Yu, Honolulu, HI (US)

(73) Assignee: Onemednet Corporation, Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,792

(22) Filed: Apr. 10, 2012

(65) Prior Publication Data

US 2012/0197664 A1    Aug. 2, 2012

Related U.S. Application Data

(60) Continuation of application No. 13/149,615, filed on May 31, 2011, now Pat. No. 8,195,483, which is a division of application No. 12/210,025, filed on Sep. 12, 2008, now Pat. No. 8,065,166.

(60) Provisional application No. 60/983,873, filed on Oct. 30, 2007.

(51) Int. Cl.
    *A61B 5/00*        (2006.01)
    *G06F 19/00*       (2006.01)
(52) U.S. Cl. .......................................................... 705/3
(58) Field of Classification Search .................... 705/2, 3
    See application file for complete search history.

(56) References Cited

U.S. PATENT DOCUMENTS

| | | | |
|---|---|---|---|
| 4,969,049 A | 11/1990 | Mitani | |
| 5,042,077 A | 8/1991 | Burke | |
| 5,319,719 A | 6/1994 | Nakazawa | |
| 5,321,520 A | 6/1994 | Inga et al. | |
| 5,384,643 A | 1/1995 | Inga et al. | |
| 5,416,602 A | 5/1995 | Inga et al. | |
| 5,557,515 A | 9/1996 | Abbruzzese et al. | |
| 5,563,962 A | 10/1996 | Peters | |
| 5,583,566 A | 12/1996 | Kanno | |
| 5,592,571 A | 1/1997 | Peters | |
| 5,606,707 A | 2/1997 | Tomassi | |
| 5,715,334 A | 2/1998 | Peters | |
| 5,724,582 A | 3/1998 | Pelanek et al. | |
| 5,734,915 A | 3/1998 | Roewer | |
| 5,740,267 A | 4/1998 | Echerer et al. | |
| 5,832,055 A | 11/1998 | Dewaele | |
| 5,867,821 A | 2/1999 | Ballantyne et al. | |
| 5,876,926 A | 3/1999 | Beecham | |
| 5,895,461 A | 4/1999 | De La Huerga | |

(Continued)

FOREIGN PATENT DOCUMENTS

| | | |
|---|---|---|
| AU | 2000042427 | 4/2000 |
| AU | 2000057454 | 6/2000 |

(Continued)

OTHER PUBLICATIONS

Partial International Search Report Received in PCT/US08/081636 Mar. 23, 2009, (including its prosecution history, the cited references and the Office Actions therein).

(Continued)

*Primary Examiner* — Gerald J. O'Connor
*Assistant Examiner* — Trang Nguyen
(74) *Attorney, Agent, or Firm* — Knobbe, Martens, Olson & Bear, LLP

(57) ABSTRACT

The disclosure herein provides methods, systems, and devices for managing, transferring, modifying, converting and/or tracking medical files and/or medical system messages. In certain embodiments, the foregoing may generally be based on requesting medical files at a first medical facility, identifying the requested medical files at a second medical facility, initiating a secure network connection between the first and second medical facility, modifying a header portion of the medical files based on patient identification information created by the first medical facility, and other processing steps.

30 Claims, 13 Drawing Sheets

U.S. PATENT DOCUMENTS

| | | |
|---|---|---|
| 5,897,989 A | 4/1999 | Beecham |
| 5,933,809 A | 8/1999 | Hunt et al. |
| 6,006,191 A | 12/1999 | DiRienzo |
| 6,047,257 A | 4/2000 | Dewaele |
| 6,128,400 A | 10/2000 | Le Beux |
| 6,157,914 A | 12/2000 | Seto et al. |
| 6,159,150 A | 12/2000 | Yale |
| 6,173,068 B1 | 1/2001 | Prokoski |
| 6,212,628 B1 | 4/2001 | Abercrombie |
| 6,219,586 B1 | 4/2001 | Sakai |
| 6,246,785 B1 | 6/2001 | Molnar |
| 6,256,613 B1 | 7/2001 | Falchuk |
| 6,260,021 B1 | 7/2001 | Wong et al. |
| 6,272,470 B1 | 8/2001 | Teshima |
| 6,275,920 B1 | 8/2001 | Abercrombie |
| 6,329,651 B1 | 12/2001 | Mestais |
| 6,397,098 B1 | 5/2002 | Uber, III |
| 6,400,996 B1 | 6/2002 | Hoffberg et al. |
| 6,494,831 B1 | 12/2002 | Koritzinsky |
| 6,529,617 B1 | 3/2003 | Prokoski |
| 6,556,698 B1 | 4/2003 | Diano |
| 6,603,494 B1 | 8/2003 | Banks |
| 6,611,806 B1 | 8/2003 | Harvey |
| 6,640,145 B2 | 10/2003 | Hoffberg |
| 6,665,820 B1 | 12/2003 | Frowein |
| 6,678,703 B2 | 1/2004 | Rothschild et al. |
| 6,678,764 B2 | 1/2004 | Parvelescu et al. |
| 6,690,761 B2 | 2/2004 | Lang |
| 6,724,933 B1 | 4/2004 | Lin |
| 6,811,310 B2 | 11/2004 | Lang |
| 6,820,100 B2 | 11/2004 | Funahashi |
| 6,826,578 B2 | 11/2004 | Anand et al. |
| 6,850,252 B1 | 2/2005 | Hoffberg |
| 6,941,313 B2 | 9/2005 | Seliger |
| 6,948,069 B1 | 9/2005 | Teppler |
| 6,970,735 B2 | 11/2005 | Uber, III |
| 6,978,268 B2 | 12/2005 | Curtis et al. |
| 6,980,987 B2 | 12/2005 | Kaminer |
| 6,993,167 B1 | 1/2006 | Skladnev |
| 7,006,881 B1 | 2/2006 | Hoffberg |
| 7,039,810 B1 | 5/2006 | Nichols |
| 7,047,235 B2 | 5/2006 | Yang |
| 7,062,105 B2 | 6/2006 | Funahashi |
| 7,068,769 B1 | 6/2006 | Weaver et al. |
| 7,111,015 B2 | 9/2006 | Aoyama |
| 7,120,225 B2 | 10/2006 | Lang |
| 7,124,442 B2 | 10/2006 | Nash-Putnam |
| 7,130,460 B2 | 10/2006 | Nakazawa |
| 7,152,785 B2 | 12/2006 | Metz |
| 7,158,692 B2 | 1/2007 | Chalana et al. |
| 7,184,814 B2 | 2/2007 | Lang et al. |
| 7,187,790 B2 | 3/2007 | Sabol |
| 7,191,463 B2 | 3/2007 | Dick |
| 7,215,803 B2 | 5/2007 | Marshall |
| 7,239,908 B1 | 7/2007 | Alexander |
| 7,251,374 B2 | 7/2007 | Niemeyer |
| 7,257,832 B2 | 8/2007 | Beane |
| 7,274,332 B1 | 9/2007 | Dupray |
| 7,298,876 B1 | 11/2007 | Marshall et al. |
| 7,302,164 B2 | 11/2007 | Wright et al. |
| 7,312,764 B2 | 12/2007 | Driver |
| 7,315,640 B1 | 1/2008 | Brady |
| 7,318,059 B2 | 1/2008 | Curtis et al. |
| 7,328,276 B2 | 2/2008 | Alisuag |
| 7,356,178 B2 | 4/2008 | Ziel |
| 7,375,364 B2 | 5/2008 | Mochizuki |
| 7,376,831 B2 | 5/2008 | Kollmyer |
| 7,386,462 B2 | 6/2008 | Silva-Craig |
| 7,388,972 B2 | 6/2008 | Kitson |
| 7,392,546 B2 | 6/2008 | Patrick |
| 7,395,214 B2 | 7/2008 | Shillingburg |
| 7,483,908 B2 | 1/2009 | Seliger |
| 7,505,810 B2 | 3/2009 | Harlev |
| 7,509,280 B1 | 3/2009 | Haudenschild |
| 7,515,954 B2 | 4/2009 | Harlev |
| 7,526,132 B2 | 4/2009 | Koenig |
| 7,555,153 B2 | 6/2009 | Martel-Pelletier |
| 7,573,034 B2 | 8/2009 | Heath |
| 7,583,827 B2 | 9/2009 | Hansen |
| 7,583,861 B2 | 9/2009 | Hanna |
| 7,594,112 B2 | 9/2009 | Patrick |
| 7,594,224 B2 | 9/2009 | Patrick |
| 7,603,547 B2 | 10/2009 | Patrick |
| 7,603,548 B2 | 10/2009 | Patrick |
| 7,613,348 B2 | 11/2009 | Eckert |
| 7,640,271 B2 | 12/2009 | Logan |
| 7,644,432 B2 | 1/2010 | Patrick |
| 7,654,463 B2 | 2/2010 | Mitamura |
| 7,657,560 B1 | 2/2010 | DiRienzo |
| 7,660,413 B2 | 2/2010 | Partovi |
| 7,660,453 B2 | 2/2010 | Lang |
| 7,664,296 B2 | 2/2010 | Tsubaki |
| 7,664,298 B2 | 2/2010 | Lang |
| 7,668,835 B2 | 2/2010 | Judd |
| 7,672,710 B2 | 3/2010 | Uber, III |
| 7,680,308 B2 | 3/2010 | Dale |
| 7,729,524 B2 | 6/2010 | Rogers |
| 7,729,597 B2 | 6/2010 | Wright |
| 7,729,752 B2 | 6/2010 | Harlev |
| 7,734,157 B2 | 6/2010 | Wright |
| 7,756,309 B2 | 7/2010 | Gholap |
| 7,756,724 B2 | 7/2010 | Gropper |
| 7,783,094 B2 | 8/2010 | Collins |
| 7,783,163 B2 | 8/2010 | Wright et al. |
| 7,783,174 B2 | 8/2010 | Wright et al. |
| 7,787,927 B2 | 8/2010 | Wood |
| 7,788,040 B2 | 8/2010 | Haskell |
| 7,799,077 B2 | 9/2010 | Lang |
| 7,801,347 B2 | 9/2010 | Wilson |
| 7,801,422 B2 | 9/2010 | Wright |
| 7,813,822 B1 | 10/2010 | Hoffberg |
| 7,818,041 B2 | 10/2010 | Kim |
| 7,822,249 B2 | 10/2010 | Garty |
| 7,823,189 B2 | 10/2010 | Patrick |
| 7,826,977 B2 | 11/2010 | Garty |
| 7,840,512 B2 | 11/2010 | Pandya |
| 7,844,087 B2 | 11/2010 | Ray |
| 7,844,571 B2 | 11/2010 | Kãnig |
| 7,849,115 B2 | 12/2010 | Reiner |
| 7,870,158 B2 | 1/2011 | DiRienzo |
| 7,872,235 B2 | 1/2011 | Rousso |
| 7,877,441 B2 | 1/2011 | Jianzhong |
| 7,881,768 B2 | 2/2011 | Lang |
| 7,889,900 B2 | 2/2011 | Weese |
| 7,898,673 B2 | 3/2011 | Randers-Pehrson |
| 7,899,687 B2 | 3/2011 | Morris |
| 7,903,113 B2 | 3/2011 | Krishnan |
| 7,904,187 B2 | 3/2011 | Hoffberg |
| 7,907,759 B2 | 3/2011 | Hundley |
| 7,907,769 B2 | 3/2011 | Sammak |
| 7,930,018 B2 | 4/2011 | Harlev |
| 7,933,472 B1 | 4/2011 | Canessa |
| 7,937,134 B2 | 5/2011 | Uber |
| 7,937,136 B2 | 5/2011 | Harlev |
| 7,944,478 B2 | 5/2011 | Shiibashi |
| 7,949,166 B2 | 5/2011 | Moriya |
| 7,949,386 B2 | 5/2011 | Buly |
| 7,953,263 B2 | 5/2011 | Okamoto |
| 7,953,475 B2 | 5/2011 | Harlev |
| 7,953,614 B1 | 5/2011 | Reicher |
| 7,957,791 B2 | 6/2011 | Harlev |
| 7,957,792 B2 | 6/2011 | Harlev |
| 7,958,063 B2 | 6/2011 | Long |
| 7,958,100 B2 | 6/2011 | Judd |
| 7,959,567 B2 | 6/2011 | Stivoric |
| 7,966,078 B2 | 6/2011 | Hoffberg |
| 7,974,714 B2 | 7/2011 | Hoffberg |
| 7,974,924 B2 | 7/2011 | Holla |
| 7,979,387 B2 | 7/2011 | Wright |
| 7,979,522 B2 | 7/2011 | Lunsford |
| 7,987,003 B2 | 7/2011 | Hoffberg |
| 7,991,610 B2 | 8/2011 | Sperschneider |
| 7,995,822 B2 | 8/2011 | Lang |
| 7,999,852 B2 | 8/2011 | Deroo |
| 8,005,688 B2 | 8/2011 | Coffman |
| 8,005,777 B1 | 8/2011 | Owen |
| 8,009,688 B2 | 8/2011 | Welin |

| | | |
|---|---|---|
| 8,065,166 B2 | 11/2011 | Maresh et al. |
| 8,090,596 B2 | 1/2012 | Maresh et al. |
| 8,099,307 B2 | 1/2012 | Maresh et al. |
| 8,108,228 B2 | 1/2012 | Maresh et al. |
| 8,121,870 B2 | 2/2012 | Maresh et al. |
| 8,131,569 B2 | 3/2012 | Maresh et al. |
| 2001/0041991 A1 | 11/2001 | Segal |
| 2002/0010679 A1 | 1/2002 | Felsher |
| 2002/0016718 A1 | 2/2002 | Rothschild et al. |
| 2002/0052851 A1 | 5/2002 | Berman |
| 2002/0073429 A1 | 6/2002 | Beane |
| 2002/0081039 A1 | 6/2002 | Funahashi |
| 2002/0083192 A1 | 6/2002 | Alisuag |
| 2002/0099571 A1 | 7/2002 | Waku |
| 2002/0194131 A1 | 12/2002 | Dick |
| 2003/0002748 A1 | 1/2003 | Funahashi |
| 2003/0074248 A1 | 4/2003 | Braud et al. |
| 2003/0126148 A1 | 7/2003 | Gropper |
| 2003/0139943 A1 | 7/2003 | Dvorak et al. |
| 2003/0177132 A1 | 9/2003 | Thomas et al. |
| 2004/0083217 A1 | 4/2004 | Brackett et al. |
| 2004/0111299 A1 | 6/2004 | Onishi |
| 2004/0120557 A1 | 6/2004 | Sabol |
| 2004/0122709 A1 | 6/2004 | Avinash |
| 2004/0122790 A1 | 6/2004 | Walker |
| 2004/0254503 A1 | 12/2004 | Sarvazyan |
| 2004/0254763 A1 | 12/2004 | Sakai |
| 2005/0063575 A1 | 3/2005 | Ma et al. |
| 2005/0071189 A1 | 3/2005 | Blake et al. |
| 2005/0071194 A1 | 3/2005 | Bormann et al. |
| 2005/0071195 A1 | 3/2005 | Cassel et al. |
| 2005/0124866 A1 | 6/2005 | Elaz |
| 2005/0133027 A1 | 6/2005 | Elaz |
| 2005/0143632 A1 | 6/2005 | Elaz |
| 2005/0158767 A1 | 7/2005 | Haskell |
| 2005/0251011 A1 | 11/2005 | Zahlmann |
| 2005/0273367 A1 | 12/2005 | Nourie et al. |
| 2006/0010015 A1 | 1/2006 | Thomas et al. |
| 2006/0015524 A1 | 1/2006 | Gardiner et al. |
| 2006/0025670 A1 | 2/2006 | Kim |
| 2006/0036468 A1 | 2/2006 | Thomas et al. |
| 2006/0053036 A1 | 3/2006 | Coffman et al. |
| 2006/0095429 A1 | 5/2006 | Abhyankar |
| 2006/0106284 A1 | 5/2006 | Shouji |
| 2006/0122865 A1 | 6/2006 | Preiss et al. |
| 2006/0143041 A1 | 6/2006 | Tipirneni |
| 2006/0149601 A1 | 7/2006 | Langhofer et al. |
| 2006/0155581 A1 | 7/2006 | Eisenberger et al. |
| 2006/0177114 A1 | 8/2006 | Tongdee et al. |
| 2006/0178910 A1 | 8/2006 | Eisenberger |
| 2006/0182324 A1 | 8/2006 | Motoki |
| 2006/0229911 A1 | 10/2006 | Gropper |
| 2006/0242148 A1 | 10/2006 | Rothpearl et al. |
| 2006/0261296 A1 | 11/2006 | Heath |
| 2006/0269106 A1 | 11/2006 | Staring et al. |
| 2006/0274928 A1 | 12/2006 | Collins |
| 2006/0282447 A1 | 12/2006 | Hollebeek |
| 2006/0285639 A1 | 12/2006 | Olivera |
| 2006/0287890 A1 | 12/2006 | Stead |
| 2007/0005713 A1 | 1/2007 | LeVasseur et al. |
| 2007/0027715 A1 | 2/2007 | Gropper |
| 2007/0027717 A1 | 2/2007 | Karamchedu et al. |
| 2007/0064984 A1 | 3/2007 | Vassa et al. |
| 2007/0064987 A1 | 3/2007 | Esham et al. |
| 2007/0090177 A1 | 4/2007 | Mitamura |
| 2007/0115999 A1 | 5/2007 | Qu |
| 2007/0133852 A1 | 6/2007 | Collins |
| 2007/0136095 A1 | 6/2007 | Weinstein |
| 2007/0192140 A1 | 8/2007 | Gropper |
| 2007/0203813 A1 | 8/2007 | DiRienzo |
| 2007/0299945 A1 | 12/2007 | Lunsford |
| 2008/0000479 A1 | 1/2008 | Elaz |
| 2008/0021740 A1 | 1/2008 | Beane |
| 2008/0040151 A1 | 2/2008 | Moore |
| 2008/0058611 A1 | 3/2008 | Tsubura |
| 2008/0063368 A1 | 3/2008 | Wright |
| 2008/0110460 A1 | 5/2008 | Elaz |
| 2008/0123925 A1 | 5/2008 | Nagatsuka |
| 2008/0131362 A1 | 6/2008 | Rousso |
| 2008/0154154 A1 | 6/2008 | Sarvazyan |
| 2008/0195249 A1 | 8/2008 | Rousso |
| 2008/0221804 A1 | 9/2008 | Jones |
| 2008/0243539 A1 | 10/2008 | Barish |
| 2008/0275309 A1 | 11/2008 | Stivoric |
| 2009/0083285 A1 | 3/2009 | Krause |
| 2009/0106051 A1 | 4/2009 | Albro et al. |
| 2009/0150292 A1 | 6/2009 | Trinh et al. |
| 2009/0177637 A1 | 7/2009 | Hollebeek |
| 2009/0238540 A1 | 9/2009 | Wright |
| 2009/0245754 A1 | 10/2009 | Wright |
| 2009/0248750 A1 | 10/2009 | Wright |
| 2009/0252479 A1 | 10/2009 | Wright |
| 2009/0252480 A1 | 10/2009 | Wright |
| 2009/0281836 A1 | 11/2009 | Velarde |
| 2009/0296540 A1 | 12/2009 | Gilbert |
| 2009/0313495 A1 | 12/2009 | Krishnan |
| 2010/0115288 A1 | 5/2010 | Monk |
| 2010/0135552 A1 | 6/2010 | Leib |
| 2010/0138240 A1 | 6/2010 | Leib |
| 2010/0138446 A1 | 6/2010 | Canessa |
| 2010/0174180 A1 | 7/2010 | Rousso |
| 2011/0010192 A1 | 1/2011 | Backhaus |
| 2011/0015941 A1 | 1/2011 | Backhaus |
| 2011/0022414 A1 | 1/2011 | Ge |
| 2011/0066449 A1 | 3/2011 | Backhaus |
| 2011/0125801 A1 | 5/2011 | Dirienzo |
| 2011/0176748 A1 | 7/2011 | Canessa |
| 2011/0238448 A1 | 9/2011 | Maresh et al. |
| 2012/0041786 A1 | 2/2012 | Yu |

FOREIGN PATENT DOCUMENTS

| | | |
|---|---|---|
| AU | 2008/318772 | 5/2009 |
| CN | 1501290 | 6/2004 |
| EP | 864959 | 9/1998 |
| EP | 1146453 A2 | 10/2001 |
| EP | 1146453 A3 | 11/2001 |
| EP | 1416419 A2 | 5/2004 |
| EP | 1420355 | 5/2004 |
| EP | 1441301 A2 | 7/2004 |
| EP | 1521200 A2 | 4/2005 |
| EP | 1621960 A2 | 2/2006 |
| EP | 1441301 A3 | 4/2006 |
| EP | 1621960 A3 | 1/2007 |
| EP | 1416419 A3 | 8/2007 |
| EP | 1521200 A3 | 10/2009 |
| EP | 2208161 | 7/2010 |
| GB | 2401459 | 11/2004 |
| GB | 2421100 | 6/2006 |
| JP | 2010/254909 | 9/1998 |
| JP | 2001/278416 | 10/2001 |
| JP | 2001/278417 | 10/2001 |
| JP | 2005/100408 | 4/2005 |
| JP | 2005/316975 | 11/2005 |
| JP | 2007/257546 | 10/2007 |
| JP | 2008/146469 | 6/2008 |
| JP | 2008/234305 | 10/2008 |
| KR | 2006-045398 | 5/2006 |
| KR | 2008-012641 | 2/2008 |
| WO | WO 96/13790 | 5/1996 |
| WO | WO 99/17218 | 4/1999 |
| WO | WO 00/62221 | 10/2000 |
| WO | WO 00/73955 | 12/2000 |
| WO | WO 01/08077 | 2/2001 |
| WO | WO 02/059814 | 8/2002 |
| WO | WO 02/093312 | 11/2002 |
| WO | WO02091129 | 11/2002 |
| WO | WO 03/021480 | 3/2003 |
| WO | WO 03/063050 | 7/2003 |
| WO | WO 03/086304 | 10/2003 |
| WO | WO 2004/104898 | 12/2004 |
| WO | WO 2005/066872 | 7/2005 |
| WO | WO 2005/091206 | 9/2005 |
| WO | WO 2006/125097 A2 | 11/2006 |
| WO | WO 2006/125145 | 11/2006 |
| WO | WO 2007/044500 | 4/2007 |
| WO | WO 2007/049996 | 5/2007 |
| WO | WO 2007/078937 | 7/2007 |
| WO | WO2007084502 | 7/2007 |

| | | |
|---|---|---|
| WO | WO 2008/008008 | 1/2008 |
| WO | WO 2008/008009 | 1/2008 |
| WO | WO 2008/067176 A8 | 6/2008 |
| WO | WO 2009/058901 | 5/2009 |
| WO | WO 2009/058901 A9 | 5/2009 |
| WO | WO 2010/126797 | 11/2010 |

OTHER PUBLICATIONS

International Search Report and Written Opinion Received in PCT/US2008/081636 Dated Jun. 29, 2009, (including its prosecution history, the cited references and the Office Actions therein).

International Search Report and Written Opinion mailed Aug. 11, 2010 regarding International Application No. PCT/US10/32281, (including its prosecution history, the cited references and the Office Actions therein).

Miller et al. "Physicians Use of Electronic Medical Records: Barriers and Solutions". In Health Affairs, vol. 23. No. 2, p. 116-226. Published Mar. 2004 [retrieved on Aug. 3, 2010]. Retrieved from the Internet <URL: http://www.wpmassociates.com/healthcare/articles/physician_use_EMR.pdf>.

Written Opinion of the International Searching Authority issued as part of the International Preliminary Report on Patentability on May 4, 2010 regarding International Application No. PCT/US2008/081636.

Letter from the applicant to the European Patent Office dated Jul. 19, 2010 regarding European Patent Application No. 08843992.2.

Figure 6

Medical Records Request Form

| | | Request Notes — 628 |
|---|---|---|
| Select medical facility to receive medical records from: | | |
| Institution State | | |
| Institution Name | | |
| Patient Information | | |
| Source Patient MRN | | |
| Destination Patient MRN | | |
| Patient First Name | | |
| Patient Last Name | | |
| Patient Middle Name | | |
| Patient Date of Birth | | |
| Patient Phone | | |
| Patient SSN Last 4 Digits | | |
| Display Request | | |
| Submit Request | | |

| Medical Image Header / Medical System Message Header | |
|---|---|
| 902 PatientName | Joe Doe |
| 904 PatientID | 21977 |
| 906 PatientBirthDate | 19880101 |
| 908 ImageType value | ORIGINAL |
| 910 value | PRIMARY |
| 912 value | RECON TOMO |
| 914 value | EMISSION |
| 916 InstanceCreationDate | 20060707 |
| 918 InstanceCreationTime | 20060707 |
| 920 InstanceCreationUID | 20060707 |
| 922 AcquisitionDate | 20060707 |
| 924 AccessionNumber | 06036567NUTIWB |
| 926 Modality | NW |
| 928 Manufacturer | GE MEDICAL SYSTEMS |
| 930 InstitutionName | GENERAL UNIV. HOSPITAL |
| 932 Station Name | hserver1 |
| 934 StudyDescription | User&Oncology&WholeBody TL201 |
| 936 AuditTrail | Image transferred from St. Johns …. |
| 938 | … |

Figure 12

Transfer Summary

From Stanford University  on 11/27/2007  To Mallinckrodt Institute

| | | |
|---|---|---|
| 00-23-25 | MRN | M123456 |
| Flintstone | Last Name | Flintstone |
| Fred | First Name | Fred |
| Wilfred | Middle Name | Wilfred |
| 11/1/2007 | DOB | 11/1/2007 |
| 235295 | Accession # | A12232 |

451 Images Transferred Securely in 17 Min 12 Seconds

1200

METHODS, SYSTEMS, AND DEVICES FOR MANAGING TRANSFER OF MEDICAL FILES

CROSS-REFERENCE TO RELATED APPLICATIONS

This application is a continuation of U.S. patent application Ser. No. 13/149,615, titled METHODS, SYSTEMS, AND DEVICES FOR TRANSFERRING MEDICAL FILES, filed May 31, 2011, which is also a divisional of U.S. patent application Ser. No. 12/210,025, now U.S. Pat. No. 8,065,166, titled METHODS, SYSTEMS, AND DEVICES FOR MANAGING MEDICAL IMAGES AND RECORDS, filed Sep. 12, 2008, which claims the benefit under 35 U.S.C. §119(c) of U.S. Provisional Application No. 60/983,873, titled METHODS, SYSTEMS, AND DEVICES FOR TRANSFERRING MEDICAL IMAGES AND RECORDS, filed Oct. 30, 2007. Each of the foregoing applications is hereby incorporated by reference herein in its entirety.

BACKGROUND

1. Field

Embodiments of the invention relate to the field of data management, and, in particular, to methods, systems, and devices for managing medical images and records data.

2. Description of the Related Art

With the development of new technologies, medical images and/or records are increasingly created and stored electronically. For example, medical images are frequently created and stored in digital form versus on hard-copy films. The same is generally true for various medical records. Despite such advancements, hard-copies of medical image and record files are nonetheless physically transferred by courier. Alternatively, medical image and record files are copied onto an electronic storage medium, such as a CDROM, and the storage medium is physically transferred from one medical facility to another.

SUMMARY

Advancements in technology make it possible to electronically transfer medical images, records, and/or medical system messages between and/or among medical professionals, medical facilities, medical systems, and/or healthcare systems using a permission-based on-demand transfer methodology as described herein. In certain embodiments, the transfer of medical images, records, files, medical system messages, and/or examinations involves the use of central authentication through a main server system, a web-based work flow management system, and/or a smart local client server system. The capability of electronically transferring medical image and record files not only enables the electronic transfer of such files, but also enables off-site viewing and reporting, off-site backup for redundancy and disaster recovery, and/or other tele-diagnosis and telemedicine scenarios.

In one embodiment, a method of electronically transferring medical files from a source medical facility to a destination medical facility comprises receiving a request to transfer at least one medical file from the source medical facility, wherein the request comprises at least patient information, and a first encryption key for establishing a secure network connection; establishing and/or accessing a secure network connection between the source medical facility and the destination medical facility with coordinated encryption keys and/or paired keys; receiving the at least one medical file from a source database for medical files; transferring the at least one medical file over the secure network connection to the destination medical facility; terminating the secure network connection after said transferring. The method of electronically transferring medical files can also comprise modifying a header portion of the at least one medical file to remove a first patient identification and replace the first patient identification with a second patient identification, wherein the first patient identification is assigned by the source medical facility and the second patient identification is assigned by the destination medical facility. The method of electronically transferring medical files can also comprise modifying the header portion of the at least one medical file to remove a first accession number and replace the first accession number with a second accession number, wherein the first accession number is assigned by the source medical facility and the second accession number is assigned by the destination medical facility; and storing the at least one medical file in a storage database for medical files. The method of electronically transferring medical files can also comprise inserting in the header portion a first accession number to substitute a second accession number existing in the header portion; and storing the at least one medical file in a storage database for medical files. In certain embodiments, the coordinated encryption keys and/or paired keys can be the first encryption key and a second encryption key, wherein the first encryption key is received by the destination facility and the second encryption key is received by the source medical facility.

In other embodiments, the source database is a picture archiving and communication systems (PACS) and/or an image server in the above method of electronically transferring medical files, for example, image files. In the above method of electronically transferring medical files, the source database can also be a radiology information system, wherein the sending further comprises creating an Observation/Results Message (OBX), and/or equivalent message or system communication, or the like, to transmit the medical file, for example, medical report files, from the radiology information system. In the above method of electronically transferring medical files, for example, image files, the storage database can be a PACS and/or an image server. In the above method of electronically transferring medical files, for example, medical report files, the storage database can be a radiology information system, wherein the storing further comprises receiving an OBX, and/or equivalent message or system communication, or the like, to store the medical file in the radiology information system.

In other embodiments, a method of electronically transferring medical files from a source medical facility to a destination medical facility comprises receiving an instruction and/or message and/or other system communication to receive at least one medical file from the source medical facility, wherein the instruction comprises at least patient information, and a first encryption key for establishing a secure network connection; establishing a secure network connection between the destination medical facility and the source medical facility with the first encryption key and a second encryption key, for example, the source medical facility having the second encryption key; receiving the at least one medical file from the source medical facility over the secure network connection; and terminating the secure network connection after said receiving. The method of transferring medical files can also comprise modifying a header portion of the at least one medical file to remove a first patient identification and replace the first patient identification with a second patient identification, wherein the first patient identification is assigned by the source medical facility and the second patient identification is assigned by the destination medical facility.

The method of transferring medical files can also comprise further modifying the header portion of the at least one medical file to remove a first accession number and replace the first accession number with a second accession number, wherein the first accession number is assigned by the source medical facility and the second accession number is assigned by the destination medical facility. The method of transferring medical files can also comprise inserting in the header portion a first accession number to substitute a second accession number existing in the header portion; and/or storing the medical file in a storage database for medical files.

In other embodiments, a method of electronically transferring medical files from a source medical facility to a destination medical facility comprises receiving an instruction and/or message and/or other system communication to transfer at least one medical file from the source medical facility, wherein the instruction and/or message and/or other system communication comprises at least patient information, and a first encryption key for establishing a secure network connection; establishing a secure network connection between the source medical facility and the destination medical facility with the first encryption key and a second encryption key; and receiving the at least one medical file from a source database for medical files. The method of electronically transferring medical files can also comprise modifying a header portion of the at least one medical file to add an entry comprising audit trail data to record the transfer of the at least one medical file; transferring the at least one medical file over the secure network connection to the destination medical facility; and terminating the secure network connection after said transferring.

In other embodiments, a system for electronically transferring medical files from a source medical facility to a destination medical facility comprises an instruction management module configured to process an instruction and/or message and/or other system communication to receive at least one medical file from the source medical facility, wherein the instruction and/or message and/or other system communication comprises at least patient information, and a first encryption key for establishing a secure network connection; a communications module for establishing a secure network connection between the destination medical facility and the source medical facility with the first encryption key and a second encryption key, wherein the at least one medical file is transferred over the secure network connection; a filter module configured to modify a header portion of the at least one medical file to add an entry comprising audit trail data to record the transfer of the at least one medical file; and a storage module configured to determine whether to store the at least one medical file in at least a PACS, an image server, a radiology information system, or a hospital information system, wherein the determination is based on a file type of the at least one medical file.

In other embodiments, a method for transferring medical files from a source medical facility to a destination medical facility comprises reviewing a request to transfer at least one medical file from the source medical facility to the destination medical facility; locating the at least one medical file in a database accessible by the source medical facility, wherein the database is at least a PACS, an image server database, a radiology information system, or a hospital information system; sending an approval to a main server system to approve the transfer of the at least one medical file, wherein the sending causes transferring of the at least one medical file from the source medical facility to the destination medical facility, and modifying a header portion of the at least one medical file to remove a first patient identification and replace the first patient identification with a second patient identification, wherein the first patient identification is assigned by the source medical facility and the second patient identification is assigned by the destination medical facility; and receiving an acknowledgement communication indicating that the at least one medical file was transferred between the source medical facility and the destination medical facility. In other embodiments of the above method for transferring medical files, the locating comprises manually, or semi-automatically, or automatically locating the at least one medical file by a film librarian.

In other embodiments, a system for electronically transferring medical files from a source medical facility to a destination medical facility comprises a user interface module configured to receive an approval communication from a user to transfer the at least one medical file, wherein the user manually locates the at least one medical file; a communications module for sending a request to the destination medical facility based on the approval communication, wherein the request comprises at least patient information, and a first encryption key for establishing a secure network connection between the destination medical facility and the source medical facility with the first encryption key and a second encryption key; wherein the sending causes receiving of the at least one medical file at the destination medical facility, and modifying of a header portion of the at least one medical file to remove a first patient identification and replace the first patient identification assigned by the source medical facility with a second patient identification assigned by the destination medical facility. In certain embodiments, the at least one medical file is located semi-automatically or automatically by the system, and the resulting medical files can be displayed to the user for selection and/or approval.

In certain embodiments, the system for electronically transferring medical files from a source medical facility to a destination medical facility comprises storing data in various data fields and/or tags and/or private tags in the electronic data file of the medical files. For example, the data stored may include without limitation a source medical facility identification number, a source medical facility patient identification, a date when the medical file was transferred, a film librarian identification number that authorized the transfer, a destination medical facility identification number, a destination medical facility patient identification, or any other type of data. In certain embodiments, multiple data fields and/or tags and/or private tags are stored in the electronic data file as the medical files are transferred between different medical facilities. In certain embodiments, the various data fields and/or tags and/or private tags can represent a digital fingerprint and/or can be used as a file integrity checkpoint and/or can be used as an audit trail to reconstitute and/or investigate where the medical files have been transferred.

In certain embodiments, a system for electronically transferring medical files from a source medical facility to a destination medical facility comprises a procedure mapping module configured to map, translate, or rename the code and/or name of a medical procedure performed at the source medical facility into the procedure code and/or name used by the destination medical facility. The procedure mapping module can be configured to use a standardized mapping table or a standardized intermediary code system to map, translate, or rename the code and/or name of a medical procedure performed at the source medical facility into the procedure code and/or name used by the destination medical facility. In certain embodiments, there is a mapping table at/for the source medical facility that can be used to map, translate, or rename the code and/or name of a medical procedure performed at the source medical facility into the standardized procedure code and/or name set forth in the standardized mapping table or standardized intermediary code system. In certain embodiments, there is a mapping table at/for the destination medical facility (and/or the main server system) that can be used to map, translate, or rename the standardized procedure code and/or name set forth in the standardized mapping table or standardized intermediary code system into the procedure code and/or name used by the destination medical facility.

In certain embodiments, a computer-implemented method of electronically transferring medical system messages from a source medical facility to a destination medical facility, the method comprises: receiving an instruction and/or communication to receive at least one medical system message from the source medical facility, wherein the instruction and/or communication comprises at least patient information, and a first encryption key for establishing a secure network connection; accessing a secure network connection between the destination medical facility and the source medical facility using paired encryption keys comprising at least the first encryption key; receiving the at least one medical system message from the source medical facility over the secure network connection; and terminating the secure network connection after said receiving.

In certain embodiments, the computer-implemented method for transferring medical system messages, further comprises: analyzing the message type of the at least one medical system message; determining whether the message type is compatible with at least one hospital system at the destination medical facility, wherein the hospital system comprises at least one of a radiology information system, hospital information system, an image server, or other medical system; converting based on said determining the at least one medical system message into a second message type that is compatible with at least one hospital system; and transmitting the converted at least one medical system message to the appropriate hospital system.

In certain embodiments, a computer-implemented method for controlling a permission-based workflow process for transferring medical files from a source medical facility to a destination medical facility, the method comprises: reviewing a request to transfer at least one medical file from the source medical facility to the destination medical facility, wherein the request further comprises a criteria for the at least one medical file; locating medical files in a database accessible by the source medical facility that possibly satisfies the criteria, wherein the database is at least a picture archiving and communication system, an image server database, a radiology information system, or a hospital information system or other medical system; causing to display to a film librarian the located medical files that possibly satisfies the criteria; receiving from the film librarian a selection of at least one of the located medical files; and sending an approval to a main server system to approve the transfer of the at least one selected medical file, wherein the sending causes transferring of the at least one selected medical file from the source medical facility to the destination medical facility.

In certain embodiments, a computer-implemented method for preventing data loss of medical files at a medical facility, the computer-implemented method comprises: receiving notification from at least one of a radiology information system, a hospital information system, a picture archiving and communication system, an image server, and other medical system that a medical file has been created or modified; obtaining the medical file from the at least one radiology information system, hospital information system, picture archiving and communication system, image server, or other medical system; accessing a secure network connection between the medical facility and a storage facility using paired encryption keys; and transferring automatically the medical file from the remote server to the storage facility.

In certain embodiments, a computer-implemented method for transferring and managing medical files at a medical facility to enable teleradiology, the computer-implemented method comprises: receiving at a source medical facility notification from at least one of a radiology information system, a hospital information system, a picture archiving and communication system, an image server, and other medical system that a medical file has been created or modified; obtaining the medical file from the at least one radiology information system, hospital information system, picture archiving and communication system, image server, or other medical system; analyzing the medical file to determine based on a criteria whether to transfer the medical file to a destination medical facility that provides at least one of outsourced radiology film interpretation, analysis, and other medical services; transferring the medical file from the source medical facility to the destination medical facility based on the analyzing. In certain embodiments, the criteria comprises at least a time period for transferring all medical files to the destination medical facility, a time period for storing said medical files at the destination medical facility, a medical expertise required to review the medical file, or an availability of medical professionals at the source medical facility.

In certain embodiments, a computer-implemented method for verifying and approving a government required release form comprises: receiving an electronic copy of an executed government required release form from a patient; analyzing a bar code on the executed government required release form to determine the identity of the patient associated with the government required release form; correlating the identity obtained from the bar code with at least one medical file associated with the identity of the patient; verifying using an optical character recognition module a signature on the executed government required release form with prior signatures stored in a database; and sending an approval communication based on said verifying to a remote server at a source medical facility to allow a transfer of the at least one medical file from the source medical facility to a destination medical facility.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIG. 6. depicts an example of one embodiment of a screen view associated with requesting medical files through the medical image and record files transfer system of FIG. 1.

FIG. 9. depicts an example of one embodiment of a header portion associated with a medical image or medical record file or medical system message.

FIG. 12. depicts an example transfer summary image.

DETAILED DESCRIPTION OF THE EMBODIMENTS

Figure 1:
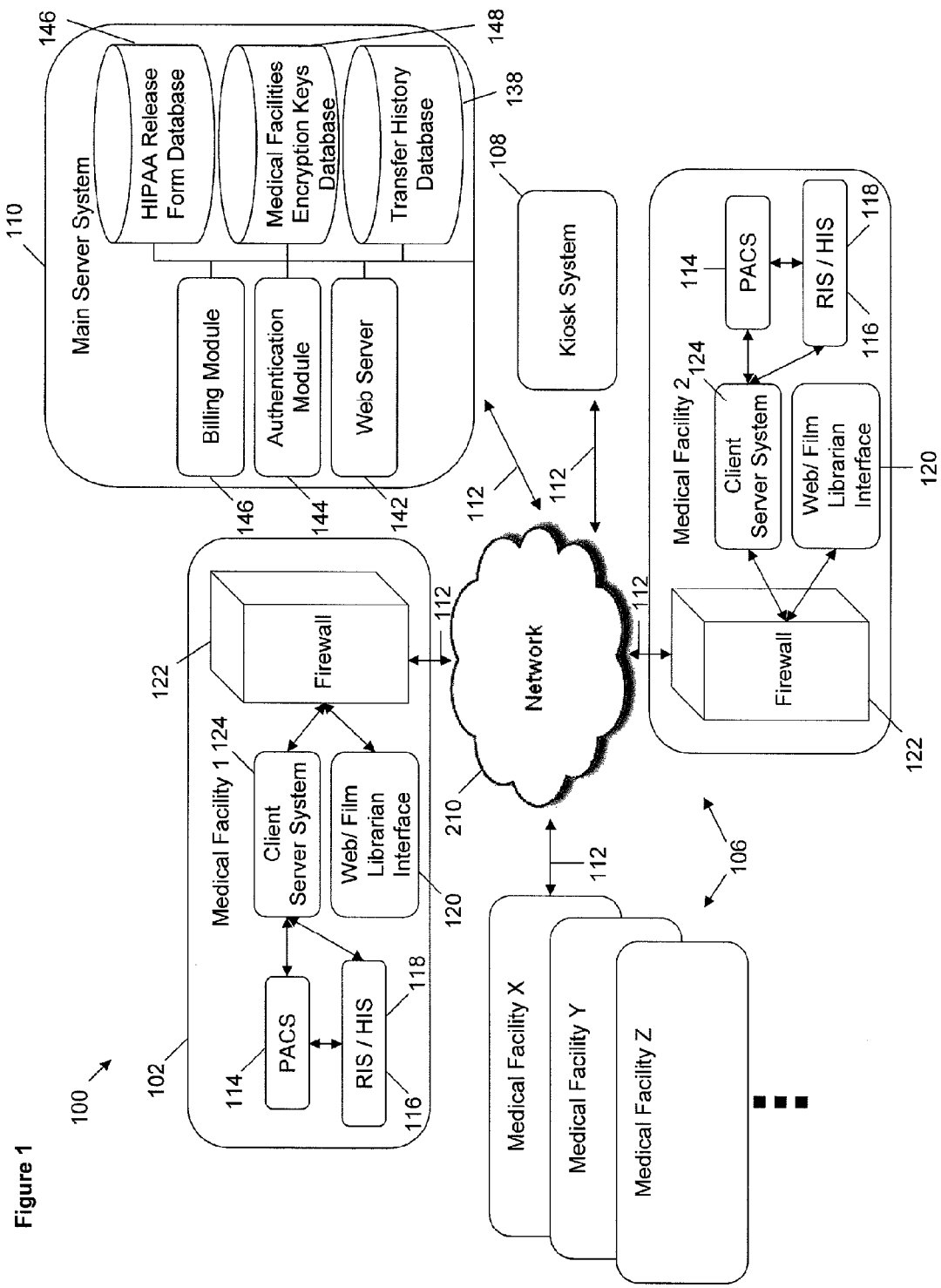
FIG. 1. is a block diagram depicting a high level overview of one embodiment of a system for managing medical image, medical system messages, and/or record files between medical facilities.

Embodiments of the invention will now be described with reference to the accompanying figures. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the inventions herein described.

As used herein, the terms "images," "records," "medical reports" and "medical files" may be used interchangeably, and the foregoing terms comprise without limitation medical images, medical records, medical reports (signed and unsigned), medical files, body dimension data, studies, any type of laboratory reports and/or results, pathology images, reports, and results, hospital notes, consults, or any other type of data, report, or results that are stored in a hospital information system (HIS), and other medical data or other patient data. The foregoing terms can also include without limitation data, reports, and/or results generated in the ambulatory setting, for example, electronic medical record (EMR) to EMR communications, or information transferred, generated, created, and/or accessed in relay health type systems that manage patient communications, and other type of medical messaging and/or communication between any types of systems.

The terms "hospital" or "medical facility" as used herein are interchangeably, and both terms comprise without limitation hospitals, private doctors' offices, medical imaging facilities, clinics, emergency and/or urgent care centers, mobile care centers, medical kiosk stations, computer stations of medical professionals, both at homes and at offices, and other medical facilities. In certain embodiments, the term "medical facility" also comprises retail outlets (both online and physical retail stores), manufacturers, and the like. In certain embodiments, the term "medical facility" also comprises but is not limited to third party individuals, consultants, contractors, and/or outsourcing facilities, for example, Night-Hawk Radiology Services® or the like.

As used herein the terms "film librarian" and "medical personnel" or "medical professional" are interchangeably used herein, and the foregoing terms comprise but are not limited to personnel that store and control access to patient medical image and/or record files, doctors, nurses, medical staff, physician aids, medical secretaries, physician assistants, or any other medical professional with access and/or authorization to create, locate, and/or match patient medical images and/or record files.

The term "transaction history information" as used herein comprises but is not limited to information about the medical facility that sent the medical file (for example, name of the medical facility, the unique medical facility identification, medical facility contact information); information about the medical facility that received the medical file (for example, name of the medical facility, the unique medical facility identification, medical facility contact information); the medical professionals and/or film librarian involved in the requesting and/or sending of the medical file; the date and time the medical file was received; and other similar information, which may sometimes be referred to or known as transaction history information. In certain embodiments, the foregoing can be used as audit trail data.

As used herein, the interchangeable terms "examinations" and "medical history information" comprise without limitation verbal and/or written physician/medical professional notes, diagnoses, treatments, prescribed drugs or treatments, allergies, reactions, prior or scheduled operations or procedures, instructions, observations, analysis or interpretation of test results, medical images or the like, laboratory and/or test results, or the like.

The terms "Health Level 7" or "HL7" as used herein refer to an ANSI accredited standard developed to allow transfer of data between different systems in healthcare. This standard for transferring data operates at the top level of the open system integration model, or at the application layer. While many medical facilities use this standard, other standards exist. Accordingly, the foregoing terms are broad terms that also refer to other standards for managing data between different healthcare systems, and the systems and methods disclosed herein can be used with, applied to, and/or operate in an environment using HL7 or any other standard for managing data between healthcare system.

The term "Picture Archiving and Communication System" and "PACS" as used herein refer to systems and devices for the acquisition, archival and retrieval of digital images over a computer network, for diagnosis and review at workstations. In certain embodiments, PACS can be configured to interface or communicate directly with a Hospital Information System (HIS) and/or Radiology Information System (RIS) using an HL7 connection. In certain embodiments, a PACS can communicate with a RIS or HIS through a PACS Broker. A PACS broker is a device that allows the PACS to interface with an HIS or RIS. In certain embodiments, a PACS can comprise, without limitation, for example, a worklist broker, an image server, an archive manager; display workstation software, and other components. In certain embodiments, a PACS is connected to an image server.

As used herein, the term "managing," or "transferring" are broad interchangeable terms, and include without limitation managing, transferring, facilitating the transferring, causing the transferring, having something transferred, sending, transmitting, causing the transmitting, or the like.

The terms "client server system," "remote server system," and "medical data transfer server" are broad interchangeable terms, and refer without limitation to computing systems and/or to systems that are involved in the process of processing and/or transferring medical files or the like, and/or controlling a workflow process for processing and/or transferring medical files. In certain embodiments, such computing systems are located at the medical facility and can communicate with the medical facility systems, such as PACS, RIS, HIS, and the like. Alternatively, such computing systems are located at a central facility and/or a hosting facility and/or a third party facility that may be located separate and apart from the medical facility. In certain embodiments, the computing system can act as a virtual remote server system that can communicate with the systems (for example, PACS, RIS, HIS, and the like) at and/or connected to the medical facility that is being served by the remote server system.

It is recognized that the term "remote" may include data, objects, devices, components, and/or modules not stored locally, that is not accessible via the local bus. Thus, remote data may include a device which is physically stored in the same room and connected to the computing system via a network. In other situations, a remote device may also be located in a separate geographic area, such as, for example, in a different location, country, and so forth.

The terms "message," "medical system message," and "medical system communication" are broad interchangeable terms, and refer without limitation to information and/or messages sent between and/or to hospital systems, for example, RIS, HIS, PACS, image servers, or other hospital systems. For example, a message can include but is not limited to a HL7 message or other equivalent message or system communications. Other examples of a medical system message may include but are not limited to EMR to EMR communications, or information transferred, generated, created, and/or accessed in relay health type systems that manage patient communications, and other type of medical messaging and/or communication between any types of systems.

The disclosure herein provides methods, systems, and devices for managing, transferring, modifying, converting and/or tracking medical files and/or medical system messages. In certain embodiments, the foregoing may generally be based on requesting medical files at a first medical facility, identifying the requested medical files at a second medical facility, initiating a secure network connection between the first and second medical facility, modifying a header portion of the medical files based on patient identification information created by the first medical facility, and other processing steps.

With the development of new technologies, medical images and/or records are increasingly created and stored electronically. Electronic medical images and records data are in certain instances reviewed by medical personnel on a picture archiving and communication systems (PACS), which are computers and/or networks dedicated to the storage, retrieval, distribution and presentation of medical images and records. Generally, the medical images and records data are stored in an independent format, wherein the most common format for storing medical images, and in some cases medical records, is DICOM (Digital Imaging and Communications in Medicine).

In certain PACS, there is software and/or hardware that prevents doctors from viewing multiple electronic files containing medical images and records wherein the electronic files are associated with different patient identification numbers. Such patient identification numbers, also known as a medical record numbers (MRN), are generally stored in the header portion of the medical images and/or records files. This is generally a safety mechanism that prevents medical professionals from comparing data from two different patients. This mechanism operates effectively when each patient possesses one identification number.

In certain instances, patients have multiple identification numbers because patients often visit multiple hospitals or other medical facilities. For example, patients move from one locality to another; or patients seek second opinions from doctors at different medical facilities; or patients visit different doctors specializing in different medical fields as patients move through various stages of life or treatment. Generally each doctor and/or medical facility has a unique patient identification numbering scheme or system.

Accordingly, a patient's medical images and/or records at one facility are associated with one patient identification number whereas the same patient's medical images and/or records at another facility are associated with a different patient identification number. Therefore, PACS that have the safety mechanism described above prevent medical professionals from conducting a side-by-side review of the medical images and/or records associated with different identification numbers even though the images and/or records correspond to the same patient. A medical professional using a PACS in conjunction with the methods, systems, and devices described herein can conduct a side-by-side review of the medical images and/or records associated with different identification numbers provided, however, that the images and/or records correspond to the same patient.

In one embodiment, medical facilities are equipped with a system that allows each facility to transfer medical files from a source medical facility to a destination medical facility. During the transfer of the medical files, the system is configured to dynamically change or add or modify the patient identification information in the header portion of each medical image and/or record file to the patient identification information that the destination medical facility has assigned to the patient. After changing, adding, or modifying the patient identification information in the header portion, the medical image and/or record files are stored in the medical facilities databases for medical professionals to review and analyze these files through a PACS or other workstation computer. By modifying the patient identification information in the header portion, a PACS or other workstation will recognize that the newly stored files correspond to the patient's previously stored files, and therefore a PACS or other workstation will allow medical professionals to conduct a side-by-side analysis of the newly stored files with the previously stored files.

FIG. 1 is a block diagram illustrating a high level overview of one embodiment of a medical image and record files transfer system 100. In the depicted embodiment, a first medical facility 102 is connected through a network 210 to a plurality of other medical facilities 106, a kiosk system 108, and a main server system 110.

Figure 3:
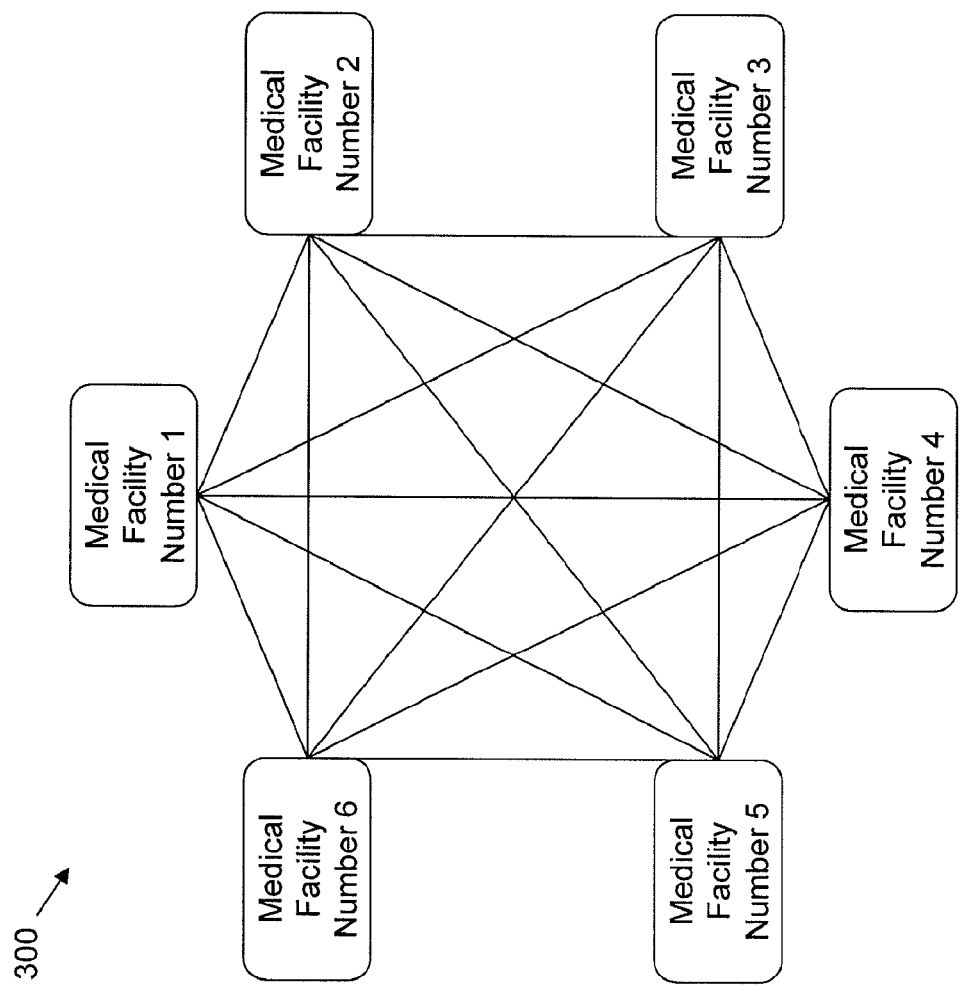
FIG. 3. is a block diagram depicting one embodiment of a data network employed by the medical image and record files management system.

The network 210 may include one or more of internet connections 112, secure peer-to-peer connections, secure socket layer (SSL) connections over the internet, virtual private network (VPN) connections over the internet, or other secure connections over the internet, private network connections, dedicated network connections (for example, ISDN, T1, or the like), wireless or cellular connections, or the like or any combination of the foregoing. In a preferred embodiment, the medical facilities are connected to each other through a mesh network 300 wherein each medical facility is capable of connecting to every other medical facility through an on-demand, and/or ad-hoc, and/or available when needed, and/or non-persistent, permission based SSL or VPN or other secure connections over the internet, as shown in FIG. 3.

At each medical facility, there may be a PACS 114, a radiology information system (RIS) 116, a hospital information system (HIS) 118, an image server, a web interface and/or a film librarian interface 120, a firewall 122, and a client server system 124. PACS 114 allow medical professionals to view medical images and records stored in various systems including in a RIS 116 and/or HIS 118. A RIS is generally used by radiology departments to store, manipulate and distribute patient radiological data and possibly images, and generally comprises patient tracking and scheduling, result reporting, and image tracking capabilities. A RIS can also comprise, without limitation, for example, the capability of creating and editing and finalizing reports and tracking of radiology information, for example, contrast usage, or the like. A HIS is an integrated information system designed to manage the administrative, financial and clinical aspects of a hospital or other medical facility.

Figure 1A:
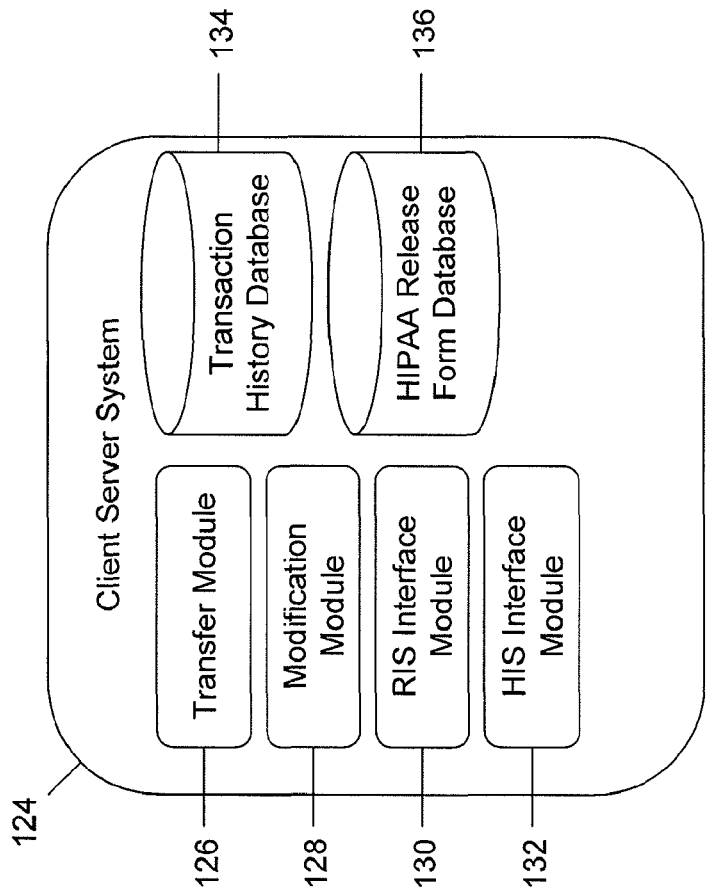
FIG. 1A. is a block diagram depicting a high level overview of one embodiment of a client server system for managing medical image, medical system messages, and/or record files between medical facilities.

In certain embodiments, the client server system 124, as depicted in FIG. 1A, comprises but is not limited to a transfer module 126, a modification module 128, a RIS interface module 130, a HIS interface module 132, a transaction history database 134, and a HIPAA release form (as used herein the term "HIPAA release form" is a broad term that generally refers to any kind of release form requested or/and required by law/statute, government entity, insurance entity, medical facility, medical professional, business entity, private/public entity, or the like) database 136. The transfer module 126 is configured to establish a secure network connection between another medical facility based on instruction information received from the main server system 110. In certain embodiments, the transfer module 126 is configured to establish the secure network connection based on an encryption key received from the main server system 110. The transfer module 126 can establish network connections serially or simultaneously. In certain embodiments, the client server system 124 comprises, or is connected to, or can electronically access a CDROM, DVD, Blu-ray, and/or other media burner for writing data onto, and/or reading data from a CDROM, DVD, Blu-ray disc, and/or other storage media.

The modification and/or filter module 128 is configured to modify the header portion of the medical files received from other medical facilities. In certain embodiments, the modification module 128 is configured to modify the patient identification information stored within the header portion of the medical files, and/or insert the patient identification number used by the medical facility where the client server system is located. In certain embodiments, the client server system 124 obtains the patient identification number to be inserted in the header file from the MS and/or the HIS systems by using the MS interface 130 module and/or the HIS interface module 132 and/or other interface modules. In other embodiments, any portion of an electronic file and/or medical system message (such as HL7) may be modified.

The transaction history database 134 is configured to record the date and time of the transfer in or out of the client server system 124, the medical facilities involved in the transfer, the medical files transferred, and other related transfer history data. In certain embodiments, the client server system 124 is configured to allow a medical professional to search and/or retrieve data from the transaction history database 138. In certain embodiments, a medical facility key obtainable from the main server system 110 is necessary in order to gain access and the ability to search and/or retrieve data from the transaction history database 134.

The HIPAA release form database 136 is configured to receive and store HIPAA release forms from the main server system. In one embodiment, the transfer module 126 verifies that that a patient HIPAA release form is stored in the HIPAA release form database 136 to determine whether the transfer module 126 is authorized to transfer related medical records to another medical facility. In other embodiments, the main server system 110 is configured to search the HIPAA release form database 140 before displaying a request for medical files on a film librarian interface 120. In certain embodiments, the main server system 110 is configured to attach or link the appropriate HIPAA release form, located within the HIPAA release form database 140, to the request for medical files so as to allow a film librarian to view the release form while reviewing the request for medical files. In other embodiments, a film librarian interface 120 is configured to allow a film librarian to search the HIPAA release form database 136, 140 to determine whether the film librarian is authorized to transfer a medical file to destination medical facility. In certain embodiments, the client server system is configured to allow a medical professional to search and/or retrieve data from the HIPAA release form database 136, 140. In certain embodiments, a medical facility key obtainable from the main server system 110 is necessary in order to gain access and the ability to search and/or retrieve data from the HIPAA release system 136, 140. In certain embodiments, the transaction history database 126 and the HIPAA release form database 136, 140 are different tables within the same database.

Referring to FIG. 1A, in certain embodiments, the client server system 124 is a smart local computer system that resides at the medical facility, and alternatively, the client server system 124 is not located at the medical facility but rather is located at a separate central hosting facility that is accessible by medical professionals. The client server system 124, whether local at the medical facility or at a central hosting facility, can also comprise network connections to the various computer systems within the medical facility. Such network connections allow the smart client server system, for example and among other things, to: establish connections with the main server system 110 and other client server systems 124; encrypt and decrypt data received and sent over a network connection; query PACS, RIS, HIS, and/or image server systems at the medical facility; and/or cause medical files, examinations, and other data to be stored in PACS, RIS, HIS, and/or image server systems at the medical facility. In one embodiment, the system allows for the client server system 124 to interface with medical professionals at the medical facility; and/or control a work flow process for transferring patient medical files, examinations, and other data between medical facilities.

Turning again to FIG. 1, a PACS 114 (or a separate image server) generally stores and archives medical images and/or records using a database or other data repository, for example, a redundant array of independent disks (RAID) system thereby allowing medical professionals to locate and retrieve, receive, access, or accept medical files at a later date. The web interface and/or film librarian interface 120 may take on various forms. In one preferred embodiment, the web interface and/or film librarian interface 120 is a web browser configured to connect and interact with the main server system 110. The web interface enables a medical professional to send a request for medical images and/or records to the main server system 110. The film librarian interface 120 allows medical professionals to receive and review requests for medical images and/or records. The film librarian interface 120 also allows the medical professional to approve or deny requests for medical images and/or records. In one embodiment, the web interface and the film librarian interface 120 do not directly connect to the client server system 124 to ensure network security of the client server 124 and the other medical facility servers. In general, the firewall 122 operates to limit and/or reduce access to files stored within a computer network, such as the local area network (LAN) generally existing at each medical facility, from remotely located machines. In other embodiments, the firewall 122 is within the client server system 124.

A kiosk system 108, or a plurality of kiosks, connects to the network 210 to communicate with the main server system 110, and to allow patients to interact with the main server 110. In certain embodiments, the kiosk system 108 or like systems can be configured, for example, to allow patients to generate requests for medical files to be transferred from one medical facility/medical professional to another medical facility/medical professional, and/or allow patients to provide approval for transferring medical files from one medical facility/medical professional to another medical facility/medical professional. For example, the kiosks 108 allow patients to submit to the main server system 110 HIPAA (Health Insurance Portability and Accountability Act) release forms, which are necessary to allow one medical facility to release medical records to another medical facility. The main server system 110 is configured to connect to the kiosk 108 to receive HIPAA release forms and store the forms in the HIPAA release form database 140 located in the main server system 110. The main server system is configured to verify the receipt of an executed HIPAA release form before releasing medical files, and, in certain embodiments, the main server system 110 is configured to send a copy of the HIPAA release form to the source medical facility such that copy of the form can be stored in the HIPAA release form database 136 at the source medical facility. In certain embodiments, the main server system 110 is configured to transfer an executed HIPAA release form to a destination medical facility for storage.

Generally, the kiosk system 108 comprises a computer having memory and a storage medium, a display, a keyboard, and a network connection. In certain embodiments, the kiosk system 108 comprises a scanner for scanning and creating a digital file of HIPAA release forms received from patients. In other embodiments, the kiosk system 108 comprises an input device configured to allow patients to write and input their signature into the kiosk system 108 thereby providing authorization to release their medical files. In other embodiments, the kiosk system 108 comprises a camera for obtaining a digital image of a patient using the kiosk system 108 thereby allowing for visual verification of the patient that is releasing medical files to another medical facility. In certain embodiments, the kiosk 108 is a home computer, personal computer, handheld device, or other user access point.

The main server system 110 connects to the client server systems 124 at the medical facilities and the kiosk systems 108 through the network 104. In a preferred embodiment, the main server system 110 comprises but is not limited to a web server 142, an authentication module 144, a transfer history database 138, a billing module 146, a HIPAA release form database 140, and a medical facility keys database 148. In certain embodiments, the main server system 110 can be configured, for example, among other things, to: act as a central authentication manager that allows client server systems 124 to communicate with other client server systems 124; control a work flow process for transferring patient medical files, examinations, and other data between medical facilities; build a knowledge database that facilitates the locating and/or transferring of medical files, examinations, and/or other data; and/or enable billing processes for each transfer of medical files, examinations, and/or other data. In certain embodiments, medical facilities encryption keys database 148, the transaction history database 138, and/or the HIPAA release form database 140 are different tables within the same database.

The web server 142 may comprise, for example, an Apache HTTP Server configured to serve web pages and web applications. In a preferred embodiment, the web server 142 operates to provide and interact with the web interface and the film librarian interface 120 at the medical facilities. In other embodiments, the web server 142 operates to provide and interact with patients using a kiosk 108. The web server 142 is configured to receive requests for medical files and direct the request to the authentication module for further processing. Based on the request, the authentication module 144 identifies the medical facility that the request should be sent to and pushes the request through the web server 142 to be displayed on the film librarian interface 120 such that the film librarian can review the request.

If the film librarian approves the request, the approval is sent through the film librarian interface 120 to the web server 142, which directs the approval to the authentication module 144 for further processing. The authentication module 144 then sends a communication to the client server system 124 at the source medical facility, wherein the communication comprises an instruction to send the requested medical files to the destination medical facility. The authentication module 144 also sends a communication to the client server system 124 at the destination module, wherein the communication comprises an instruction to receive the requested medical files from the source medical facility.

In a preferred embodiment, the communication sent by the authentication module 124 to the client server systems 124 at the destination and source medical facilities also comprise a network security key for establishing a secure network connection between the two client server systems 124. In certain embodiments, the client server systems 124 are configured to establish secure network connections sequentially or simultaneously wherein each connection uses a different network security key provided by the main server system 110. In certain embodiments, the security key provided by the main server system 110 is only or is generally valid for one use and/or for a specific period of time. Alternatively, the security key can be recycled after a period of time of non-use, and still be unique or substantially unique to allow for secure communications and/or connections. In certain embodiments, it is the authentication module 144 that determines the number times and/or the expiry of the network security key. If a transfer of medical files fails to occur, the destination and/or the source medical facilities sends a communication to the main server system 110, reporting that the medical image files were never sent and/or received. The authentication module 144, in certain instances, is configured to send another communication to the client server systems 124 at the destination and source medical facilities, wherein the communication comprises a new network security key and an instruction to send/receive the requested medical files.

The authentication module 144 also operates to record the date and time of the transfer authorization, the medical facilities involved in the transfer, the medical files transferred, and other related transfer history data into the transfer history database 138. The authentication module 144 also operates to communication/signal the billing module to bill the appropriate party for the transfer. In a preferred embodiment, the billing module 146 bills the source medical facility for each transfer of medical files. The billing module 146 can also be configured to bill the destination medical facility for each request and/or transfer of medical files into the destination medical facility. The billing module 146 can also be configured to generate a bill/invoice or transmit a bill/invoice over a network connection or through regular mail to any other party, such as an insurance company, third party invoice processing center, or the like. The billing module 146 can be configured to generate and/or transfer bills/invoices on a real time basis substantially with the completion of the transfer of medical files, or on a periodic basis, a batch basis, or the like. The billing module 146 can also be configured to generate a bill/invoice based on a per transaction/transmission basis or a subscription model.

In certain embodiments, the medical facility keys database 148 stores medical facility keys used by medical professionals to access the transaction history database 134 and the HIPAA release form database 136 stored in the client server systems 124 located at the medical facilities.

Computing System

Figure 2:
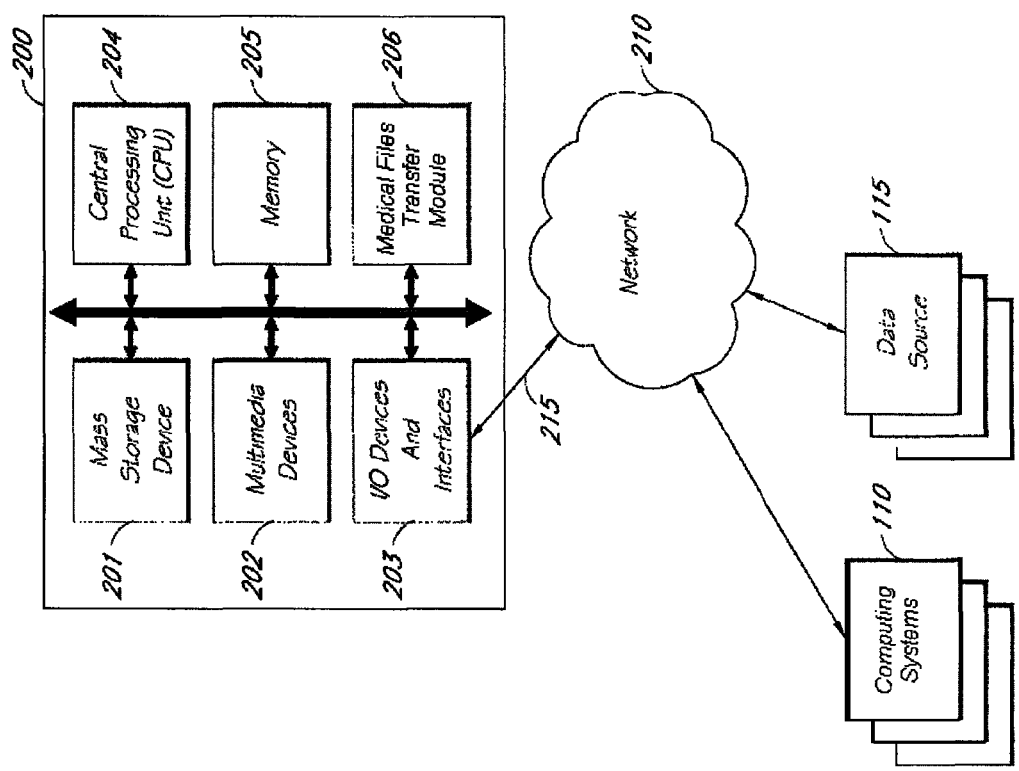
FIG. 2. is a block diagram depicting one embodiment of a computer hardware system configured to run software for implementing one or more embodiments of the medical image, medical system messages, and/or record files management system described herein.

In some embodiments, the computer clients and/or servers described above take the form of a computing system 200 shown in FIG. 2, which is a block diagram of one embodiment of a computing system that is in communication with one or more computing systems 110 and/or one or more data sources 115 via one or more networks 210. The computing system 200 may be used to implement one or more of the systems and methods described herein. In addition, in one embodiment, the computing system 200 may be configured to transfer medical files between medical facilities, including maintaining and storing medical files and executing searching and matching algorithms for identifying relevant medical files to fulfill requests for medical files. While FIG. 2 illustrates one embodiment of a computing system 200, it is recognized that the functionality provided for in the components and modules of computing system 200 may be combined into fewer components and modules or further separated into additional components and modules.

Client/Server Module

In one embodiment, the system 200 comprises a medical files transfer module 206 that carries out the functions described herein with reference to the client server systems or the main server system. The medical records transfer module 206 may be executed on the computing system 200 by a central processing unit 204 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Computing System Components

In one embodiment, the computing system 200 also comprises an individual computer, a cloud computing system, a grid computing system, and/or a mainframe computer system suitable for controlling and/or communicating with large databases, performing high volume transaction processing, and generating reports from large databases. The computing system 200 also comprises a central processing unit (CPU) 204, which may comprise a microprocessor. The computing system 200 further comprises a memory 205, such as random access memory (RAM) for temporary storage of information and/or a read only memory (ROM) for permanent storage of information, and a mass storage device 201, such as a hard drive, diskette, or optical media storage device. Typically, the modules of the computing system 200 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The computing system 200 comprises one or more commonly available input/output (I/O) devices and interfaces 203, such as a keyboard, mouse, touchpad, and printer. In one embodiment, the I/O devices and interfaces 203 comprise one or more display devices, such as a monitor, that allows the visual presentation of data to a user. More particularly, a display device provides for the presentation of GUIs, application software data, and multimedia presentations, for example. In the embodiment of FIG. 2, the I/O devices and interfaces 203 also provide a communications interface to various external devices. The computing system 200 may also comprise one or more multimedia devices 202, such as speakers, video cards, graphics accelerators, and microphones, for example.

Computing System Device/Operating System

The computing system 200 may run on a variety of computing devices, such as, for example, a server, a Windows server, a Structured Query Language server, a Unix server, a personal computer, a mainframe computer, a laptop computer, a cell phone, a personal digital assistant, a kiosk, an audio player, iPhone, and so forth. The computing system 200 is generally controlled and coordinated by operating system software, such as z/OS, Windows 95, Windows 98, Windows NT, Windows 2000, Windows XP, Windows Vista, Linux, BSD, SunOS, Solaris, or other compatible operating systems. In Macintosh systems, the operating system may be any available operating system, such as MAC OS X. In other embodiments, the computing system 200 may be controlled by a proprietary operating system. Operating systems control and schedule computer processes for execution, perform memory management, provide file system, networking, and I/O services, and provide a user interface, such as a graphical user interface (GUI), among other things.

Network

In the embodiment of FIG. 2, the computing system 200 is coupled to a network 210, such as a local area network (LAN), wide area network (WAN), or the Internet, for example, via a wired, wireless, or combination of wired and wireless, communication link 215. In a preferred embodiment, the network is a mesh network 300 wherein each computing system is capable of connecting to every other computing system or data source through an on-demand or non-persistent permission based secure socket layer (SSL) or virtual private network (VPN) or other secure connections over the internet, as shown in FIG. 3. The network 210 communicates with various computing devices and/or other electronic devices via wired or wireless communication links. In the embodiment of FIG. 2, the network 210 is communicating with one or more computing systems 110 and/or one or more data sources 115.

Access to the medical files transfer module 206 of the computer system 200 by computing systems 110 and/or by data sources 115 may be through a web-enabled user access point such as the computing systems' 110 or data source's 115 personal computer, cellular phone, laptop, or other device capable of connecting to the network 210. Such a device may have a browser module is implemented as a module that uses text, graphics, audio, video, and other media to present data and to allow interaction with data via the network 210.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 203 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive inputs/signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 200 may comprise a physical or logical connection established between a remote microprocessor and an individual computer, a cloud computing system, a grid computing system, and/or a mainframe host computer for the express purpose of uploading, downloading, or viewing interactive data and databases on-line in real time. The remote microprocessor may be operated by an entity operating the computer system 200, including the client server systems or the main server system, an/or may be operated by one or more of the data sources 115 and/or one or more of the computing systems. In some embodiments, terminal emulation software may be used on the microprocessor for participating in the micro-mainframe link.

In some embodiments, computing systems 110 who are internal to an entity operating the computer system 200 may access the medical files transfer module 206 internally as an application or process run by the CPU 204.

User Access Point

In one embodiment, a user access point comprises a personal computer, a kiosk, a laptop computer, a cellular phone, a GPS system, a Blackberry® device, a portable computing device, a server, a computer workstation, a local area network of individual computers, an interactive kiosk, a personal digital assistant, an interactive wireless communications device, a handheld computer, an embedded computing device, iPhone, or the like.

Other Systems

In addition to the systems that are illustrated in FIG. 2, the network 210 may communicate with other data sources or other computing devices. The computing system 200 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

Human and/or Electronic Process

Figure 4:
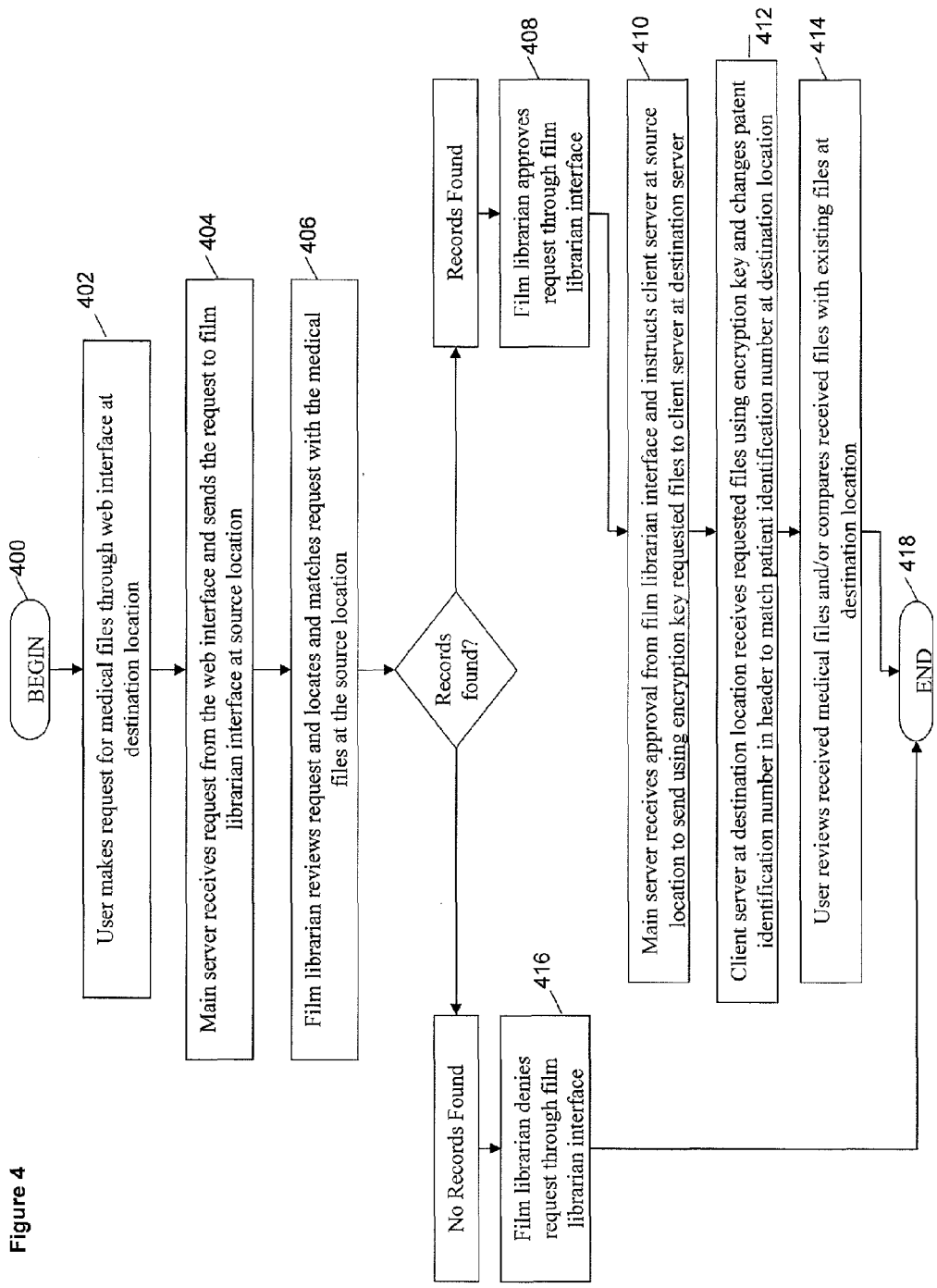
FIG. 4. depicts a simplified example of one embodiment of requesting and managing medical image and record files using the medical image and record files management system of FIG. 1.

FIG. 4 is a simplified example of one embodiment of requesting and transferring medical image and record files using the medical files transfer system of FIG. 1. At block 400 a medical professional at a first medical facility makes a request for at least one medical file by completing a request form through the web interface. The first medical facility is also known as the destination medical facility because the medical file will be transferred to the destination medical facility. In contrast, the medical facility that receives the request for the medical file is also known as the source medical facility.

On the request form, the medical professional provides patient information related to the patient, and medical facility information related to both the destination and source medical facilities. For example, the patient information may comprise, but is not limited to, the patient's name, the patient's identification number at the destination medical facility, the patient's identification number at the source medical facility, the patient's age, sex, disease type, address, date of birth, social security number, or the like. The medical facility information may comprise, but is not limited to, the name of the medical facility, identification number of the medical facility, the location of the medical facility, the division or branch office of the medical facility, the telephone number of the medical facility, or the like. In one embodiment, the PACS, RIS, HIS, and/or other local hospital systems can comprise the same functionality as the film librarian interface such that the PACS, HIS, and/or other local hospital systems can be configured to automatically generate a request for medical files, wherein the request is sent to the main server system an application programming interface (API). For example, a doctor reviewing medical files on a PACS can in-context (meaning while reviewing medical files for a particular patient) generate a request for related medical files that are available at other medical facilities by using the interface of the PACS. In certain embodiments, the generated request from PACS, RIS, HIS, and/or other local hospital systems can submitted, transmitted, and/or communicated through a http:// or https:// connection, or URL request/message, internet connection, wireless connection to the main server, the client server system, and/or the film librarian interface system. In certain embodiments, the generated request from the PACS, RIS, HIS, and/or other local hospital systems can be transmitted, communicated, and/or submitted through a messaging protocol (for example, HL7) over any kind of network.

The web interface sends the patient information and the medical facility information to the main server, wherein the main server system determines where the request should be sent. After identifying the appropriate medical facility (the source medical facility) to send the request, the main server system at block 404 sends the request to the film librarian interface corresponding to the source medical facility.

In a preferred embodiment, the film librarian or other medical personnel at block 406 reviews the request on the film librarian interface, and attempts to locate and match the patient name and source patient identification number provided in the request form. In certain circumstances, the medical professional searches a PACS, a RIS, a HIS, or the like to locate medical files associated with the information provided in the request form. In certain embodiments, the system semi-automatically and/or automatically conducts a search and/or matches the patient name and source patient identification number provided in the request form and/or searches a PACS, a RIS, a HIS, or the like to locate medical files associated with the information provided in the request form. In certain embodiments, the system presents or causes to display match information (for example, exact and/or near matches) to the film librarian for review and/or approval and/or selection. The medical professional then determines whether the source medical facility possesses medical files corresponding to the provided patient information.

If the medical professional locates and matches the provided patient information with medical files at the source medical facility, the medical professional approves the request form by interacting with the film librarian interface. The film librarian interface sends the approval communication as well as the matching information to the main server at block 408. The matching information can comprise but is not limited to the patient identification number assigned by the source medical facility, and/or names or other identifications to locate the requested medical files. At block 410, the main server system then instructs the client server system at the source medical facility to send, transmit, or transfer the appropriate medical record files to the client server system located at the destination medical facility. At block 412, the main server system also instructs the client server system located at the destination medical facility to receive, access, accept, or retrieve the appropriate medical files from the client server system at the source medical facility.

In other embodiments, the main server system stores or saves the matching information for future use. For example, if a future request is received by the main server system, and the request comprises substantially the same or similar patient information and/or medical files/examinations, and/or MRN's, the main server system can be configured to automatically match and/or locate the requested medical files based on the previously saved matching information and/or user-configurable matching criteria and/or other algorithm. For example, the main server system can be configured to build over time a knowledge database of matching patient identification numbers, MRN's, locations of medical files/examinations, or the like. In certain embodiments, the knowledge database is generated or updated periodically or in real time based on data mining of the Transaction History Database or by querying various attached and/or connected client server systems at medical facilities. Using the knowledge database, the main server system can be configured to send, transfer, or cause to display a listing of all or substantially all the medical files/examinations at all or substantially all the medical facilities equipped with a client server system. For example, for a specific patient identification number used by one medical facility, the main server system can be configured to generate a listing of all known patient identification numbers assigned to the patient at other medical facilities, and generate a listing of all or substantially all known medical files/examinations available at the various medical facilities. In certain embodiments, the knowledge database is generated from data received and/or stored in the client server system. In other embodiments, the main server system is configured to generate the listing information by retrieving the patient information from the multiple client server systems in real time or periodically based on a batching process.

In other embodiments, the locating and matching is performed automatically by the main server system or the client server system, and not by a medical personnel operating through a film librarian interface. In this embodiment, the main server system is configured to send a request for medical files to the client server system at the source medical facility. The client server system automatically attempts to match and/or locate the medical files associated with the patient information provided in the request form via user-configurable matching criteria and/or other algorithm. In searching for the medical files, the client server system connects to the medical facility's PACS, image server, RIS, HIS, or other database system where patient medical files are stored.

If a match that satisfies a minimal threshold is found, then the request form is approved automatically by the client server system, and/or may be presented, displayed to the film librarian for approval, and a communication is sent back to the main server. The main server system then instructs the client server system at the source medical facility to send the appropriate medical record files to the client server system located at the destination medical facility. The main server system also instructs the client server system located at the destination medical facility to receive the appropriate medical files from the client server system at the source medical facility.

Accession Number Creation

To track medical files received at a destination medical facility, accession numbers are created for each medical file received. The accession number not only tracks the medical file within a medical facility, but also an accession number is used to link related portions of a medical file that are related but stored in different databases. For example, an accession number can link a medical image stored in the image database with a corresponding doctor's report that is stored in a RIS and/or HIS system because the same accession number has been stored in the header portion of both medical image file and the doctor's report file.

In one embodiment, after the medical file has been transferred from the source medical facility to the destination medical facility, the client server system directly creates an accession number in the RIS and/or HIS and/or PACS systems at the destination medical facility, wherein the accession number relates to the medical files that have been received. In other embodiments, the accession number is created before the medical files have been transferred but after the client server has instructed by the main server system to receive medical files from another medical facility.

In one embodiment, the process of creating an accession number occurs directly between the client server system and the RIS and/or HIS and/or PACS system when the client server system has full and open access to the RIS and/or HIS and/or PACS systems. Where the client server system does not have full and open access to the RIS and/or HIS and/or PACS system, the client server system, in certain embodiments, is configured to create an Order Message (ORM), or equivalent message or the like, that is sent to the RIS and/or HIS and/or PACS systems, which causes the RIS and/or HIS and/or PACS systems to create an accession number for the medical files that were received, and returns the accession number to the client server system.

In the HL7 Standard, an ORM message is any request for materials (for example, 500 ml of 2.5% saline) or services (for example, a range of motion study, an EKG, a lipid panel, and the like). Orders are usually for a particular patient. The transmission of clinical orders occurs between the application placing the order (the placer) and the clinical application filling the order (the filler). Accordingly, the placer in this embodiment is the client server system at the destination medical facility and the filler is the RIS and/or the HIS system at the medical facility.

Header Modifications and Image Conversions

The client server system at the destination medical facility is configured to modify the header portion of the medical files to ensure that the medical files are compatible with the patient identification numbering system, and the other systems at the destination medical facility. In certain embodiments, the client server system modifies the header portion of the medical files by removing, modifying, substituting, or, adding the patient identification number that corresponds to the source medical facility and inserts, modifies, substitutes, or, adds the patient identification number utilized by the destination medical facility.

In certain embodiments, the client server obtains the patient identification number from the RIS and HIS systems associated with the destination medical facility. In some embodiments, the client server obtains the patient identification number from the main server system. In certain embodiments, the main server system provides this information while instructing the client server system at the destination medical facility to receive, retrieve, access, or accept medical files from the source medical facility. In other embodiments, the client server system at the source medical facility modifies the header portion of the medical files to comprise the patient identification number provided by the destination medical facility, wherein such modification at source medical facility can occur prior to the transfer of the medical file from the source to the destination medical facility.

In some instances, the destination medical facility provides the patient identification number directly to the source medical facility. In other instances, the patient identification number is provided to the source medical facility by the main server system. In other instances, the client server system at the source medical facility is configured to transfer a raw medical data file without a header portion, wherein the client server system at the destination medical facility is configured to add a header portion comprising information compatible with the PACS and other systems of the destination medical facility.

In certain embodiments, the client server system at the destination medical facility is configured to confirm the medical files into a format that is compatible for the PACS and other systems at the destination medical facility. For example, the client server system is configured to convert a DICOM medical image file into a JPEG medical file. Alternatively, the client server system may convert a DICOM medical image file with the image compressed in JPEG2000 to a format compatible with the target PACS or other system such as a DICOM image compressed in standard JPEG.

The client server system and/or the remote server system is configured to store the received medical files and/or examinations in the PACS, image server, RIS and/or HIS systems at the destination medical facility. A medical professional can then retrieve and view the medical files from the PACS, RIS and/or HIS systems at the destination medical facility. In certain embodiments, a user at the destination medical facility can view medical files obtained from the source medical facility side-by-side with the medical files from the destination medical facility. In certain embodiments, the client server system is configured to also store the received medical files in a patient data database within the client server system to enable medical professionals to retrieve and/or review medical files and/or examinations directly from the client server system without retrieving the information from the PACS, image server, RIS, and/or HIS systems. The client server system can be configured to store the medical files and/or examinations indefinitely or for a temporary period of time, for example, minutes, hours, days, months, or years. In certain embodiments, the client server system can be configured to control, store and/or remove medical files and/or examinations based on a policy that can be fixed and/or amended.

Transaction History Information

In one embodiment, the client server system comprises a transaction history database for tracking the transfer history of medical files. For example, the client server system is configured to record in the transfer history database the transfer of every or substantially every medical file that is transferred in and/or out of its medical facility, and such information is known as transaction history information as defined above. In certain embodiments, the transaction history information is associated and/or is assigned a unique identifier in a lookup table or the like so that the foregoing information can be recalled based on the unique identifier. The unique identifier or a reference tag is then embedded or written or stored in the header of the medical file to a form an audit trail thereby allowing medical professionals or others to later determine the origins of the file.

In certain embodiments, the client server system is configured to decipher or interpret at least a part of the foregoing unique identifiers. For example, the client server system can identify the medical facility that created the unique identifier. Based on that information the client server system and/or a medical professional can search or request to have searched the transfer history database of the medical facility that created the unique identifier to obtain the transfer history information associated with the medical file.

Instead of storing a unique identifier in the header portion of a medical file, in another embodiment, the transaction history information itself is written or added into the header portion of the medical file as text or in another data format every time or substantially every time the medical file is transferred from one medical facility to another thereby creating an audit trail. If transaction history information is in text, the transaction history information can be written with or without tags (for example, XML, HTML, and the like). In certain embodiments, the PACS or other system is configured to allow a medical professional to review and analyze the transaction history information stored in the header portion of the medical file, using a header viewer system.

In other embodiments, the client server system is configured to analyze, interpret, normalize, and/or filter the transaction history information in the header portion of a medical file, and directly store the information in RIS and/or HIS systems when the client server system has direct and open access to the RIS and/or HIS systems. In other embodiments, where the client server system does not have open and direct access to the RIS and/or HIS system, the client server system creates an Observation/Results Message (OBX), or equivalent message, system communication, or the like, comprising the transaction history information and an accession number, and sends the OBX message, or equivalent message, system communication, or the like, to the RIS and/or HIS systems which accepts and processes, and stores the message. Normalizing, as used herein, can comprise but is not limited to a method or system of analyzing the data, extracting certain recognized data elements, and assigning those data elements to a particular related data field used by the system.

In other embodiments, the transaction history information is transferred in the data portion of a medical file instead of the header portion of a medical file. The transaction history information can be stored as text in the data portion of the medical file with or without tags (for example, XML, HTML, and the like), or the transaction history information can be stored as an image in the data portion of the medical file. If stored as an image file, then the client server system is configured to modify the header portion of this medical file as disclosed herein and store the medical file in the PACS and/or image server.

In certain embodiments, the PACS and/or other systems are configured to allow a medical professional to review and analyze the transaction history information stored in the data portion of the medical file as a normal medical image or record file. PACS and/or other systems can also be configured to compare and/or review the transaction history information as an image with other medical files because the patient identification numbers do not conflict and/or are the same after the client server system inserts, overwrites, amendments, adds, and/or modifies the correct patient identification number to the header portion of the medical files.

In any transfer of medical files and/or examinations, there may be multiple series of medical files, images, reports, and/or examinations in the set. For example, a set may include without limitation a series of scout views, a series of brain window images, a set of bone window images, and/or the like. In certain embodiments, a transaction history information summary image 1200 may appear with separate series and/or set. For example, as illustrated in FIG. 12, a transaction history information summary image 1200 can be displayed at the beginning, the end, and/or at any other point of each series. In other embodiments, the transaction history summary images 1200 may appear at the beginning, end, and/or at any other point in the set. In other embodiments, the client server system is configured to analyze, interpret, filter the transaction history information in the data portion of a medical file, normalize the transaction history information, and store the normalized transaction history information in RIS and/or HIS systems at either a destination or source medical facility.

If the transaction history information is stored as text in the data portion of a medical file, then the client server system is configured to analyze, interpret, normalize, and/or filter the transaction history information in the data portion of a medical file, and directly store the information in RIS and/or HIS systems when the client server system has direct and open access to the RIS and/or HIS systems. In certain embodiments, the storing of the transaction history information in the RIS and/or HIS systems occurs by inserting the information into specific related entry fields when the client server system has open and/or complete access to the RIS and/or HIS systems.

In other embodiments, where the client server system does not have open and direct access to the RIS and/or HIS system, the client server system creates an OBX message, or equivalent message, system communication, or the like, comprising the transaction history information and an accession number, and sends the OBX message, or equivalent message, system communication, or the like, to the RIS and/or HIS systems which accept and process, and stores the message. Normalizing, as used herein, can comprise but is not limited to a method or system of analyzing the data, extracting certain recognized data elements, and assigning those data elements to a particular related data field used by the system. and/or the RIS/HIS systems as a medical file. The OBX, or equivalent message, system communication, or the like, can comprise at least the patient identification number used by the destination medical facility, the accession number and the transaction history information and the name of the medical file associated with the transaction history information.

In the HL7 Standard, an OBX is a message used to transmit a single observation or observation fragment. One mission of an OBX is to carry information about observations and results. Sometimes, the OBX segment is found as a part of an order message (ORM or RDE). In this case, the OBX carries clinical information needed by the receiving system. For example, an OBX is needed to report the menstrual phase information which should and/or could be included on an order for a pap smear to a cytology lab. The OBX message or segment can be used to contain encapsulated data, for example, a PDF document, a CDA document or a DICOM image or any of the MIME (Multimedia Internet Mail Extension) support formats such as JPEG, GIF, FAX, and the like. If the actual observation value is not sent in an OBX but exists somewhere else, the OBX message or segment can contain a reference pointer. The reference pointer can be a hyperlink which the receiving system would use to access the observation information, document, or image. The OBX segment can be used to transmit patient clinical information in a variety of formats.

In other embodiments, the client server system is configured to transfer the transactional history information by electronic mail after receiving instructions from the main server system.

Medical History Information

Transaction history information differs generally from medical history information as is defined above. In certain embodiments, the medical history information is transferred from one medical facility to another in the data portion, as opposed to the header portion, of a medical file using the various transfer methodologies described herein. The client server system at a destination medical facility is configured to receive to the medical file comprising the medical history information. In some instances, the medical history information is stored as text with or without tags (for example, XML, HTML, and the like); however, the medical history information can also be stored as an image.

If the medical history information is stored as text, then the client server system at the destination medical facility is configured to analyze, interpret, normalize, and/or filter the medical file comprising the medical history information, and/or directly store the medical history information into the RIS and/or the HIS system located at the destination medical facility. In certain embodiments, the storing of the medical history information in the RIS and/or HIS systems directly occurs by inserting the information into specific related entry fields when the client server system has open and/or complete access to the RIS and/or HIS systems.

If the client server system does not have open and/or complete access to the RIS and/or HIS systems, the client server system, in some instances, is configured to create OBX, and/or equivalent message or system communication or the like, comprising the medical history information, and sends the OBX, and/or equivalent message or system communication or the like, to the RIS and/or HIS systems such that the medical history information can be stored in the RIS and/or HIS systems at the destination medical facility. The OBX, and/or equivalent message or system communication or the like, can comprise at least the patient identification number used by the destination medical facility, the accession number, and the medical history information.

If the medical history information is stored as an image, then the client server in certain embodiments stores the image in the PACS and/or image server or RIS or HIS, assuming the target system can accept image data. The client server system is configured to modify the header portion of the medical file that comprises the medical history information by inserting or adding to the header portion the patient identification number used by the destination medical facility. In certain embodiments, the client server system is configured to directly store the modified medical file comprising the medical history information in the PACS and/or image server. In other embodiments, the client server system is configured to directly store the modified medical file in RIS and/or HIS systems where the client server system has direct and/or full access to those systems. If the client server system does not have direct and/or full access to those systems, then the client server system creates an OBX, or equivalent message, system communication, or the like, that can comprise the image, and sends the message to the PACS, RIS and/or HIS systems for processing and storage. Medical professionals with access can use PACS, RIS, and/or HIS systems thereafter to view the medical file side-by-side with other medical files for that patient stored at the medical facility because the patient identification numbers stored in the header of the medical files do not conflict and/or are the same.

In the foregoing embodiment, the medical history information can also be inserted into the header portion of the medical file instead of the data portion of a medical file. The client server system at a destination medical facility is configured to receive to the medical file comprising the medical history information in the header portion of the medical file. In some instances, the medical history information is stored as text with or without tags (for example, XML, HTML, and the like). In certain embodiments, the client server system at the destination medical facility is configured to analyze, interpret, normalize, and/or filter the header portion comprising the medical history information, and/or directly stores the medical history information into the RIS and/or the HIS systems located at the destination medical facility where the client server system has direct and/or full access to those systems. If the client server system does not have direct and/or full access to those systems, then client server system creates an OBX, or equivalent message, system communication, or the like, that comprises the medical history information, and sends the message to the RIS and/or HIS systems for processing and storage.

In other embodiments, the client server system is configured to transfer the medical history information by electronic mail after receiving instructions from the main server system.

Figure 5:
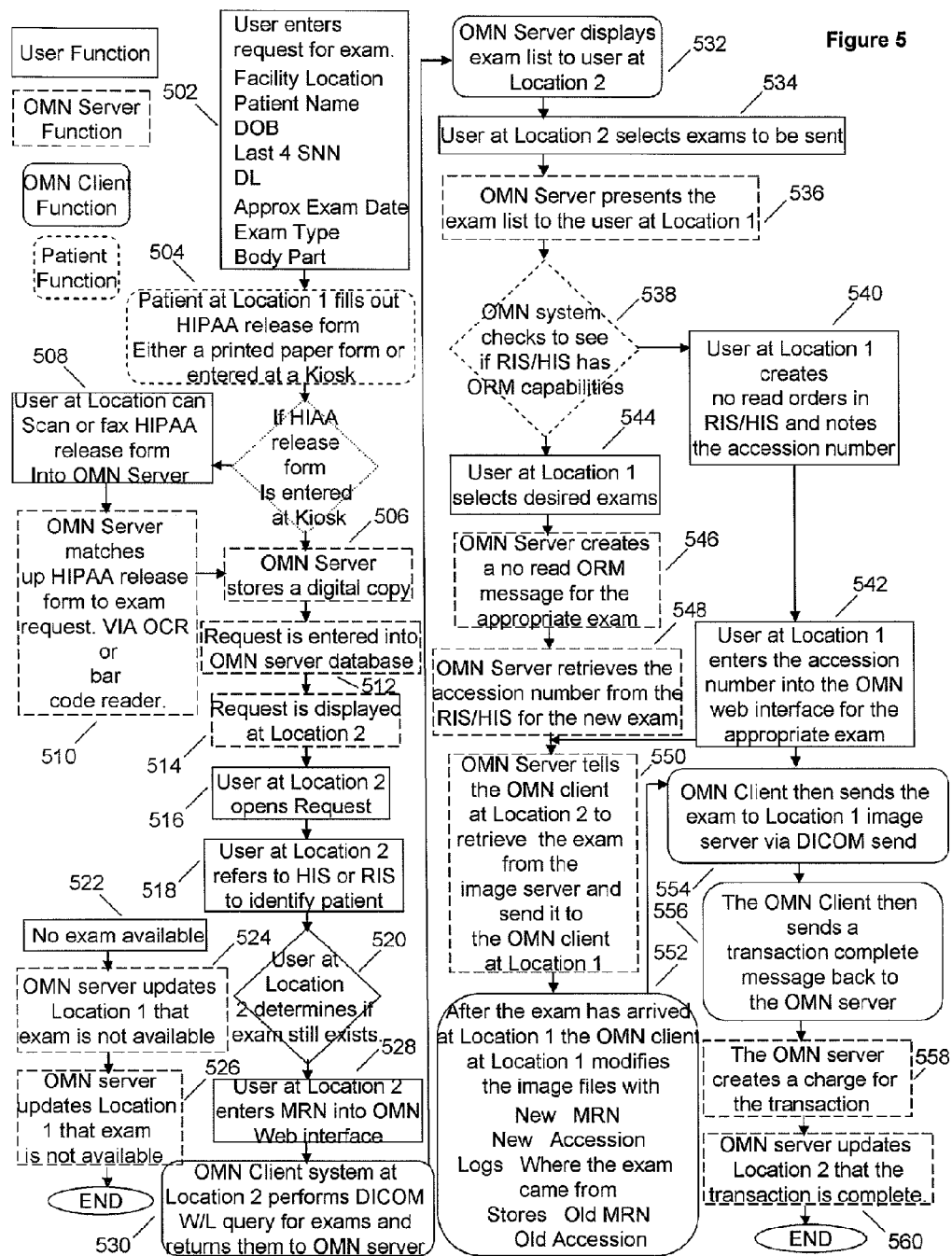
FIG. 5. depicts a detailed example of one embodiment of requesting and transferring medical image and record files using the medical image and record files transfer system of FIG. 1.

FIG. 5 depicts a detailed example of one embodiment of requesting and/or transferring medical image and/or record files using the medical image and record files transfer system of FIG. 1. At block 502, a medical professional enters a request for an exam or medical file by using the request form interface as illustrated, for example, in FIG. 6. As disclosed herein, the request form interface can take on various forms, and preferably, the request form interface is a web interface accessible from most any computer or device with network access to the web server in the main server system. The information provided by the medical professional comprises but is not limited to facility location, patient name, date of birth, last four digits of the patient's social security number, DL, approximate date of examination and/or medical file creation, examine type, body part examined, and the like.

Concurrently or sequentially, at block 504 patient completes and submits a HIPAA release form. A patient can use a kiosk system, or other user access point at the destination medical facility (or at some other location) completes and/or submits a HIPAA release form for allowing the requested medical files to be released. In certain embodiments, there is a unique bar code on the HIPAA release form to uniquely identify the HIPAA release form or to associate the HIPAA release form to a particular patient. In certain embodiments this HIPAA release form may be computer generated and downloadable from the internet or in other embodiments may be printed by the kiosk. As disclosed herein, the kiosk system or a hospital/medical facility workstation attached and/or electronically connected to the client server system can accept a paper form completed by the patient. After accepting the HIPAA release form, the kiosk can scan and/or OCR the paper form (into a PDF, TIFF, or other document/image file format) at block 506, and identify the bar code or other information on the form. In certain embodiments, the bar code is already associated with the patient, in which case, the kiosk can associate the scanned paper form with the correct patient and transfer the scanned paper form to the main server system for storage in the HIPAA release form database. In certain embodiments, the bar code is not already associated with the patient, in which case, the kiosk system instructs that the user input identification information (name, contact information, username, and/or identification code, or the like), and kiosk system verifies the information with the main server system. If the patient information is verified, then the kiosk system associates the patient identity (for example, the main server system's unique identifier, the patient identification at the source medical facility, the patient identification at the destination medical facility, or the like).

Alternatively, at block 508, the HIPAA release form can be faxed to an electronic facsimile (fax) system or other computer system that can digitize and process the fax. At block 510, the fax system can have OCR integrated into the system so that the fax system can read, interpret, and/or decipher the bar code on the HIPAA release form, thereby allowing the fax system to automatically associate the faxed HIPAA release form with the proper patient and/or request.

Alternatively, the kiosk system can allow the patient to complete the form electronically via the interface on the kiosk system. In certain embodiments, the kiosk system is configured to comprise a signature pad, wherein the patient can write or input his signature to be electronically stored in a database at the kiosk system, or in the main server system, or in the client server system at a medical facility, or printed on to a HIPAA release form. To verify the identity of the patient, the signature can be compared to prior signatures on file by the main server system or by the film librarian. The kiosk can also comprise a webcam or other video/photo input device for capturing a video or photographic image of the patient using the kiosk. The video or photographic image can be used by the film librarian to verify the identity of the patient.

In other embodiments, the kiosk system is a computer accessible by the patient, or other device accessible by the patient, such as but not limited to a handheld computer with network access to the main server system. Such computers or devices can include without limitation all or some of the features of the kiosk set forth above. Alternatively, the patient and/or the medical professional can fax, email, or otherwise transfer the HIPAA release form to the main server system for storage in the HIPAA release form database.

As disclosed herein, the main server system receives the executed HIPAA release form and the request for medical files, and matches the HIPAA release form to the request by optical character recognition (OCR) software, corresponding bar codes, or other methodology of linking the form with the request. At block 512, the main server system stores the request for medical files in the transfer history database and stores the HIPAA release form in the HIPAA release form database. At block 514, using the various methods and systems disclosed herein, the main server system displays the request for medical files on a film librarian interface at the appropriate source medical facility. At block 516, a film librarian at the source medical facility reviews the request for medical files, and at block 518 uses the MS and/or HIS interfaces available to the film librarian to identify the patient and at block 520 to locate the requested examination or medical files.

In certain embodiments, the main server system is configured to compare, using OCR software or other recognition software, the signature on the HIPAA release form to signatures previously received, stored, or recorded in the HIPAA release form database to verify the identity of the patient. The main server can also compare the photographic image or video with previously stored photographic images or videos to verify the identity of the patient. The foregoing verification steps can also be completed by the film librarian.

At block 522, if no examination or medical files that correspond to the information in the request form exist or are available, then the film librarian selects the option "no films were available" using the film librarian interface. At block 524 and 526, the response is then sent from the film librarian interface to the main server system, and the main server system displays the response on the film librarian interface at the destination medical facility, notifying the medical professional that the requested medical record file could not be found. Alternatively and/or additionally, the main server system is configured to send an email or other notification to the medical professional that created the request for the medical file. In certain embodiments, the email can be encrypted and/or protected using other secure protocols and/or means for protecting the confidential data within the email. The email can also be configured to comprise a hyperlink to a secure website (for example, requiring a username and password, encryption key, authentication and/or the like) in order to obtain, retrieve, and/or review the confidential data and/or information.

If the examination or medical files that correspond to the information in the request form do exist or are available, then the film librarian selects the option "approve" using the film librarian interface. In certain embodiments, at block 528 the film librarian interface displays the approval form wherein the film librarian enters the medical record number (MRN) into the approval form as disclosed herein and submits the information. The approval information is sent to the main server system, and the main server system sends the information to the client server system at the source system to perform a search for the medical files corresponding to the MRN's provided by the film librarian. For example, at block 530 the client server system at the source medical facility performs on a PACS and/or an image server at the source medical facility a DICOM query for examinations related to the MRN's provided by the film librarian.

If the medical records are located at the source medical facility, the main server system is notified and at block 532 the main server system displays on the librarian interface at the source medical facility the information relating to the medical files located at the source medical facility. Using the film librarian interface at block 534, the film librarian selects the examination and/or the medical files appropriate for transfer to the destination medical facility. These selections are sent from the film librarian interface and sent to the main server system, and at block 536 the main server system sends the information to film librarian interface at the destination facility so as to notify the medical professional that requested the medical files. Alternatively and/or additionally, the main server system is configured to send an email or other notification to the medical professional that created the request for the medical file.

The main server system also sends the information about the located medical files to the client server system at the destination medical facility. In certain embodiments, at block 538 the client server system performs a check to determine whether the PACS, RIS and/or HIS systems or other medical systems at the destination medical facility have ORM, and/or equivalent message or system communication or the like, capabilities.

If there are no ORM capabilities, and/or equivalent order capabilities, and/or other electronic order creation capabilities, the client server system at block 540 sends a communication to the main server system, and the main server system relays the communication to the film librarian interface the destination medical facility, instructing the film librarian to manually create an order, and/or a no read order, in the RIS and/or HIS system at the destination medical facility. The RIS and/or HIS system creates an accession number to be associated with the medical files being transferred to the destination medical facility. The film librarian at the destination facility is then presented with a list of exams available for the selected patient. This list may aggregate available studies from multiple medical facilities or may present only studies from one source medical facility, based upon whether the initial request was to one or multiple facilities or all known facilities. The destination film librarian can then select the exams and/or medical files that are appropriate and desired for transfer. At block 542, for the each exam and/or medical files selected for transfer, the destination film librarian uses the film librarian interface to select the request at issue and inserts the accession number in the request form. The film librarian interface sends that information to the main server system, and the main server system sends the information to the client server system at the destination medical facility.

If there are ORM, and/or equivalent message or system communication or the like, capabilities, the film librarian at the destination facility can then be presented with a list of exams available for the patient. This list may aggregate available studies and/or medical files from multiple medical facilities or may present only studies and/or medical files from one source medical facility, based upon whether the initial request was to one or multiple medical facilities. At block 544, the destination film librarian can then select the exams and/or medical files that are appropriate and desired for transfer. At block 546, the client server system can then create an ORM, and/or equivalent message or system communication or the like, and sends it to the RIS and/or HIS system at the destination medical facility for each exam selected. The RIS and/or the HIS system receives the ORM, and/or equivalent message or system communication or the like, creates and accession number to be associated with each of the medical files, and returns to the client server the accession number for each file. In one embodiment, at block 548, the client server system retrieves the accession number from the RIS and/or HIS system after each ORM, and/or equivalent message or system communication or the like, has been sent.

In certain embodiments, the film librarian and/or the medical professional that created the request for the medical files selects the desired medical files from those that are available, and such selection is made through the film librarian interface in some instances. In other embodiments, the medical files are automatically transferred from the source destination medical facility.

In certain embodiments, after the accession number has been created and has been obtained by the client server system at the destination medical facility, the client server system sends a communication to the main server system, and at block 550 the main server systems sends a communication to the client server system at the source medical facility, wherein the communication comprises an instruction to initiate a network connection with the destination medical facility and send the requested medical files to the destination medical facility.

In certain embodiments, the communication comprises without limitation, the instruction to retrieve selected medical files from a PACS, and/or an image server, HIS system, and/or RIS system, instructions to transfer medical files to the destination medical facility, the medical record number, the patient identification number used at the source medical facility, the medical facility identification number of the destination medical facility, the network location of the client server system at the destination medical facility, and/or a network key/encryption key for establishing a secure network connection with the client server system at the destination medical facility. In certain embodiments, the network key/encryption key is only valid and/or usable for a specific period of time, and/or can only be used once. Alternatively, the network key/encryption key can be recycled and/or reused after a period of non-use.

A similar communication is sent from the main server system to the client server system at the destination medical facility, wherein the communication comprises an instruction to accept and/or establish a network connection with the source medical facility to receive the requested medical files from the source medical facility.

In certain embodiments, the communication to the client server system at the destination medical facility comprises without limitation, the instruction to locate the accession number to be associated with the medical files, instructions to receive the medical files from the source medical facility, the patient identification number used at the destination medical facility, the medical facility identification number of the source medical facility, the network location of the client server system at the source medical facility, and/or a network key/encryption key for establishing a secure network connection with the client server system at the source medical facility.

In other embodiments, the client server system is configured with an interface device for receiving medical files from a portable storage media instead from the source medical facility through a network connection. For example, a portable storage media may comprise but is not limited to a CDROM, DVD-R, Blu-ray, USB or other memory stick, floppy diskette, a magnetic tape, or the like. In other embodiments, the client server system is configured with or is connected to an email server, wherein the client server system is configured to receive medical files through email as an attachment or a link to a network storage server or the like.

After the medical files have been received by the client server system at the destination medical facility, at block 552 the client server system, in certain embodiments, is configured to modify the header portion of the medical file to insert or add data as disclosed herein. For example, the client server system can be configured to insert or add or replace as appropriate the following information into the appropriate fields of the header portion of transferred medical files: the new medical record number used by the destination medical facility, the new accession number used by the destination medical facility, the patient identification number used by the destination medical facility, the transaction history information to record the transfer of the medical record file from the source to the destination medical facility; the old accession number used by the source medical facility, the old accession number used by the source medical facility, or any other information.

At block 554 and block 556 the client server system is configured to then store the medical record files in the appropriate database. For example, if the medical record is a DICOM image then the client server system may be configured to store the medical file in the PACS and/or image server at the destination medical facility. In other instances the medical file is a text file or a PDF file comprising a report or analysis of a medical image file, and the client server system is configured to store the medical file in the PACS, RIS and/or the HIS and/or other system at the destination medical center. As disclosed herein, the storing of the medical file in the RIS and/or the HIS system can occur directly between the client server system and the RIS/HIS system, or by the client server system creating an OBX, and/or equivalent message or system communication or the like, comprising the medical file and sending the OBX, and/or equivalent message or system communication or the like, to the RIS/HIS system for processing and storage.

In other embodiments, the client server system at the source medical facility sends the requested medical files to destination medical facility. After receiving the medical files, the client server system at the destination medical facility creates an ORM, and/or equivalent message or system communication or the like, and sends it to the PACS, RIS and/or HIS or other medical system to generate an accession number for each exam received. The PACS, RIS and/or HIS or other medical system receives the ORM, and/or equivalent message or system communication or the like, creates the accession number to be associated with each of the medical files, and returns it to the client server. The client server at the destination medical facility modifies, inserts, replaces the accession number in the header of the medical file with the newly generated accession number received by the client server system.

FIG. 6 depicts an example of one embodiment of a screen view 600 of the request form interface associated with requesting medical files through the medical image and record files transfer system of FIG. 1. The screen view can take on various forms, such as an HTML-based web interface, a java applet, a Windows interface, or the like. As disclosed herein, the requesting screen view is connected to the main server system through the network.

In this requesting screen view 600, the medical professional at the destination medical facility provides information related to the medical files being requested. For example, the information may comprise but is not limited to institution state 602, institution name 604, patient name 612, 614, 616, the patient identification number used by the source medical facility 608, the patient identification number used by the destination medical facility 610, the date of birth of the patient 618, the patient phone number 620, the medical files being requested (for example, by description, by accession number, by date and type) 628, and at least a portion of the patient's social security number 622. The medical professional can also insert notes 628 to be viewed by the film librarian at the source medical facility. After completing the requesting form, the medical professional selects the submit button 626 and the request is sent to the main server system.

Figure 7:
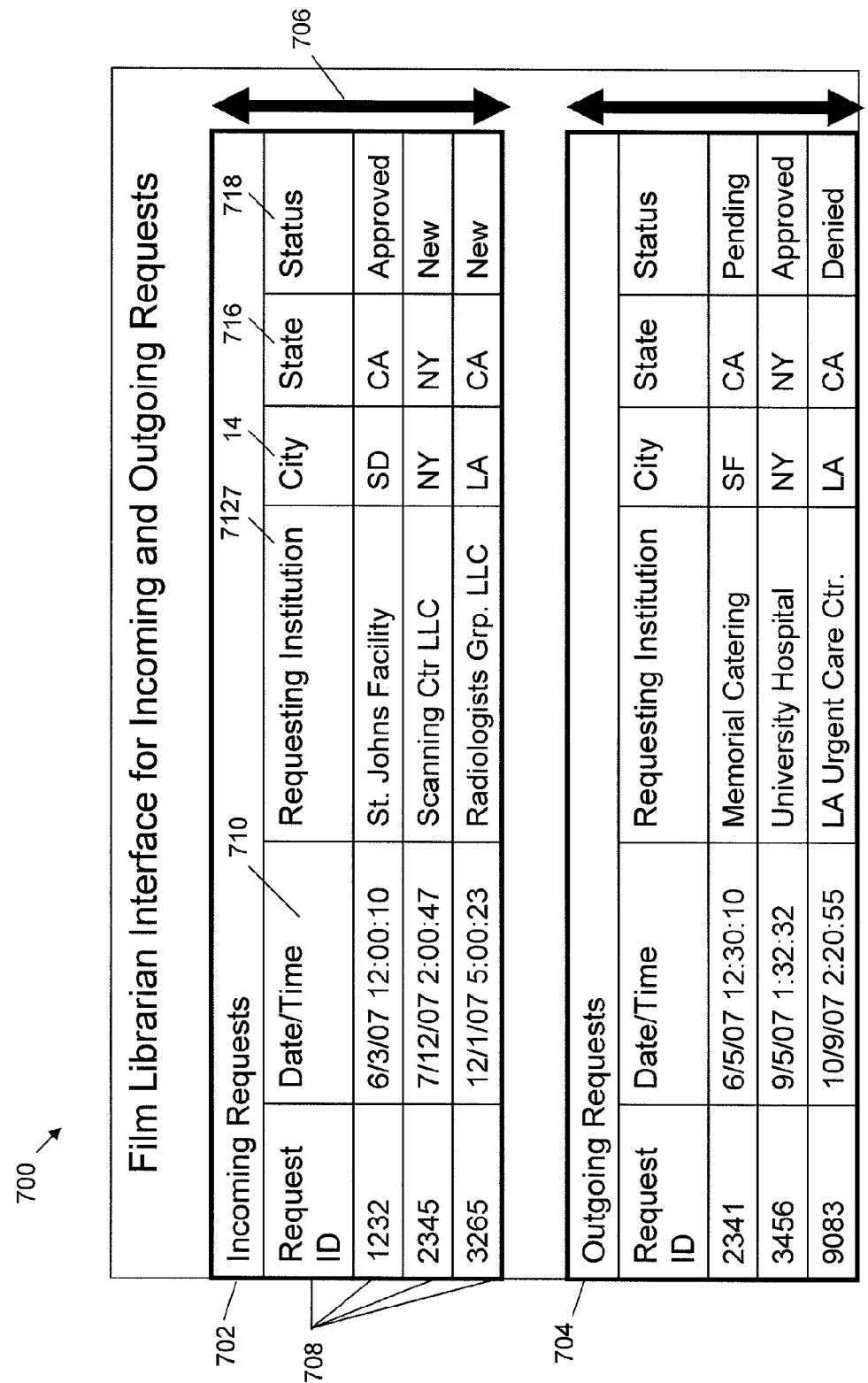
FIG. 7. depicts an example of one embodiment of a film librarian interface associated with some embodiments of the medical image and record files transfer system of FIG. 1.

FIG. 7 depicts an example of one embodiment of a film librarian interface 700 associated with some embodiments of the medical image and record files transfer system of FIG. 1. The screen view 700 can take on various forms, such as an HTML-based web interface, a java applet, a Windows interface, or the like. As disclosed herein, the film librarian interface screen view is connected to the main server system through the network.

In this film librarian interface screen view 700, the film librarian at the source medical facility is provided information related to incoming requests 702 for medical files as well as the status of outgoing requests 704 for medical files that were created by medical professionals at the source medical facility. For example, in the top portion of the screen, the film librarian is presented with incoming requests 702 for medical files from various medical facilities. The film librarian can scroll 706 through the incoming requests wherein certain information is displayed, such as the unique identification number of the request 708, the date and time of the request 710, the requesting institution 712, the city 714, state 716, and status of the request 718, or the like. For example, the status of a request could be but is not limited to new, approved, denied, and not found. The film librarian can click on any one of the requests to review the detailed information about the request.

The film librarian can utilize the request information displayed on the film librarian interface 700 to cross reference with other database interfaces accessible at the source medical facility to search for the requested medical files. If the film librarian does not locate the medical files, the film librarian can select the files not found button. If the film librarian does locate the records but the HIPAA release form cannot be located or is invalid, then the film librarian can select the denied button. If the film librarian does locate the records and the HIPAA release form can be found and/or is valid, then the film librarian hits the approve button, which launches a new screen window as shown in FIG. 8.

Figure 8:
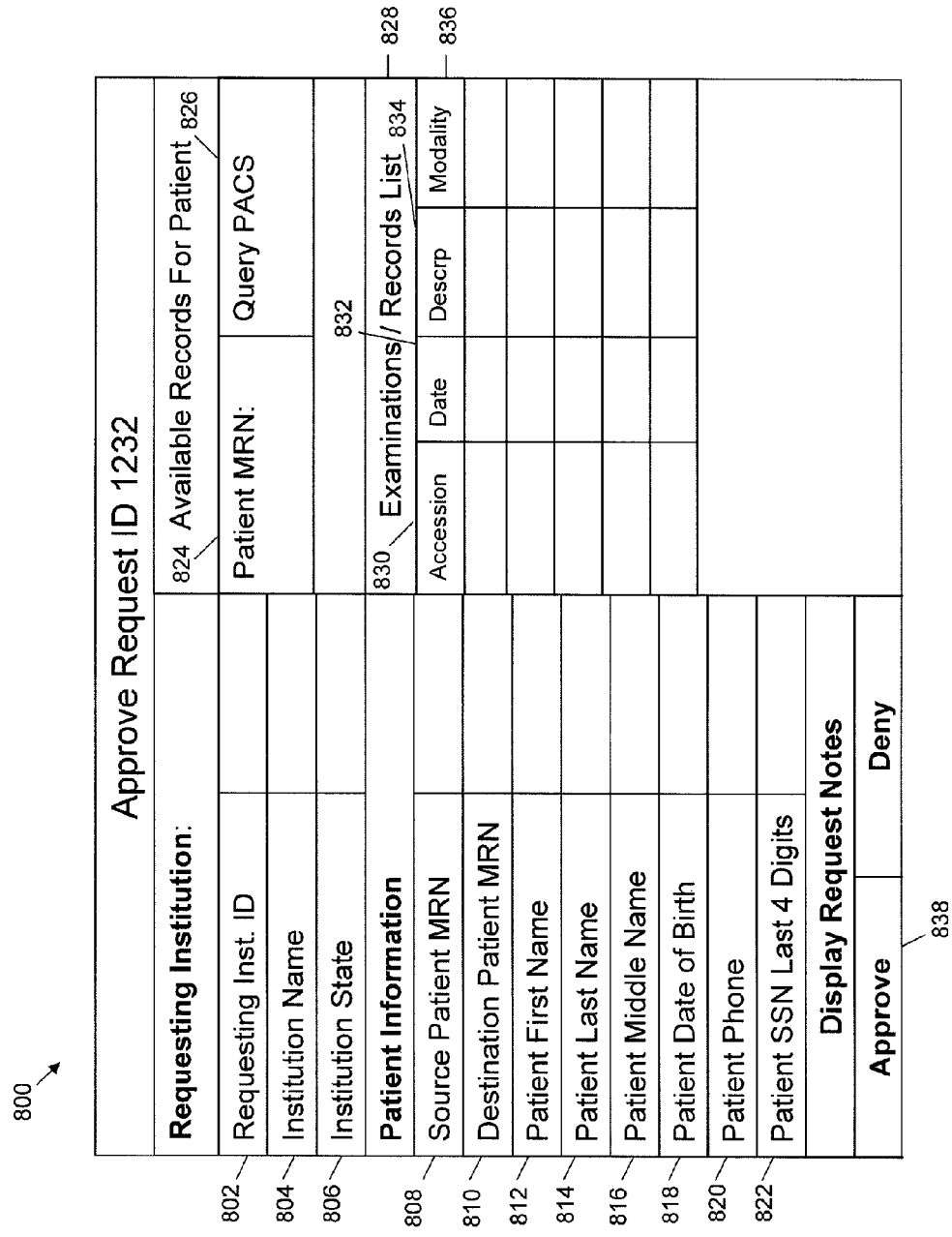
FIG. 8. depicts an example of one embodiment of a screen view associated with approving a request for medical files through the medical image and record files transfer system of FIG. 1.

FIG. 8 depicts an example of one embodiment of a screen view 800 associated with approving a request for medical files through the medical image and record files transfer system of FIG. 1. The screen view 800 can take on various forms, such as an HTML-based web interface, a java applet, a Windows interface, or the like. As disclosed herein, the approving screen view that is part of the film librarian interface is connected to the main server system through the network.

In this approving screen view 800, the information about the request for medical files and the related patient information is displayed. For example, the information comprises but is not limited to institution state 806, institution name 804, patient name 812, 814, 816, the patient identification number used by the source medical facility 808, the patient identification number used by the destination medical facility 810, the date of birth of the patient 818, the patient phone number 820, the medical files being requested (for example, by description, by accession number, by date and type), and at least a portion of the patient's social security number 822. The film librarian can also insert, input, and/or append information about the available or located medical records available for transfer 828. For example, the film librarian can input information such as accession number 830, date 832, description of the medical file 834, and modality the medical file exists 836, or the like. In certain embodiments, the system can automatically and/or semi-automatically populate, input, insert, and/or write information into the approving screen view for the film librarian to review and/or approve 838. The film librarian can also insert notes to be viewed by the medical profession at the destination medical facility.

After completing the approving form, the film librarian selects the approve button and the approval information is sent to the main server system. In certain instances, the main server system is configured to send instructions to the client server system at the source medical to send the specified medical files to the destination medical facility, and to send instructions to the client server at the destination medical facility to accept the medical files from the source medical facility. In other embodiments, the main server system is configured to present the available medical files to the film librarian at the destination medical center, wherein the film librarian at the destination medical center can select which medical files should be transferred from the source medical facility. After the medical files are selected on the film librarian interface at the destination medical facility, the selection information is sent from the film librarian interface to the main server system wherein the server system sends instructions to both the client server systems at the source and destination medical facilities as set forth above.

FIG. 9 depicts an example of one embodiment of a header portion 900 associated with a medical image or medical record file. In the header portion of a medical file, various fields can exist, for example, patient name 902, patient identification number 904, patient social security number, the medical facility that created the image or record 932, audit trail 938, medical history information, or the like. In the audit trail field, the client server system, in some embodiments, is configured to insert or add transaction information. In the medical history information field, the client server system, in some embodiments, is configured to insert or add medical history information.

Figure 10:
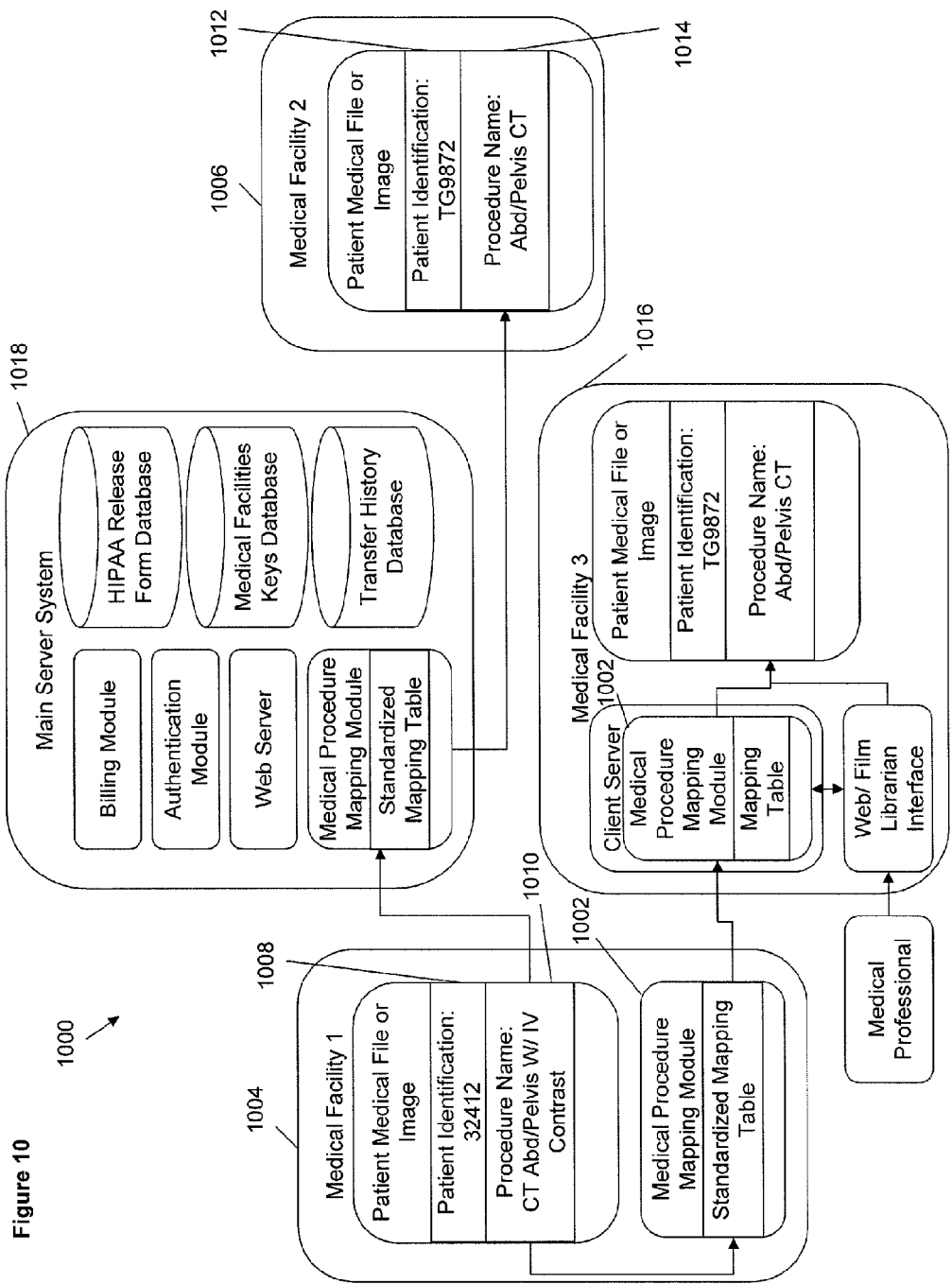
FIG. 10. depicts an example of one embodiment of a process flow diagram illustrating an example of a medical procedure mapping.

With reference to FIG. 10, an example of the medical procedure mapping module 1002 is depicted in the main server system. The medical procedure mapping module 1002 can be used to map, translate, or rename the code and/or name of a medical procedure performed at a first medical facility 1004 into the procedure code and/or name used by a second medical facility 1006. As illustrated in FIG. 10, Medical Facility 1 1004 has performed scan of Patient 32412 1008, and the procedure name for the scan is CT Abd/Pelvis w/IV Contrast 1010, which means Patient 32412 had a CT scan of his abdomen and pelvis areas with IV contrast added. Patient 32412 has authorized Medical Facility 2 1006 to access his scan; however, Medical Facility 2 1006 has a different patient identification number 1012 for the patient, and uses a different name for the medical procedure that was performed, for example, Abd/Pelvis CT w/1014.

Accordingly, and still with reference to FIG. 10, the code and/or procedure name of the scan can be changed within the header portion of the patient file for purposes of ensuring that the file is compatible with the medical systems at Medical Facility 2 1006, enabling medical professionals at Medical Facility 2 1006 to determine the contents of the medical file, conforming the file name to the consistent naming standard of Medical Facility 2, ensuring the association of the proper billing codes and/or medical reimbursement codes to the medical file, or the like. The remapping or renaming protocol can be a one-to-one mapping or a many to one mapping, or one to many mapping. For example, a one-to-one mapping is where each code and/or name of a medical procedure is mapped to one specific code and/or name. In contrast, a many-to-one mapping is where several codes and/or names of medical procedures are mapped to one specific code and/or name.

In certain embodiments, the system is configured to map medical procedure codes and/or names at destination and/or source medical facilities to a standardized mapping table and/or a standardized intermediary code system. By using a standardized mapping table and/or a standardized intermediary code system the complexity of maintaining separate mappings for each institution can be reduced. The original procedure name and/or code may in certain embodiments be stored in a DICOM tag or private DICOM tag in the header and/or displayed as in a summary image saved, stored, embedded, or burned into the image set. In certain embodiments, the medical procedure mapping module automatically maps, translates, and/or renames the source procedure code and/or name to the code and/or name of the medical procedures used at the destination medical facility, possibly through the standardized intermediary code system described above, and stores the data in the PACS, RIS and/or HIS systems at the destination medical facility.

Regarding FIG. 10, in certain embodiments, the medical procedure mapping module 1002 is located at the medical facility in the client server system 1004. After receiving the medical file from Medical Facility 1 1004, the client server system at Medical Facility 3 1016 processes the header portion of the medical file using the medical procedure mapping module. The medical procedure mapping module identifies the "CT Abd/Pelvis W/IV Contrast" code 1010 and/or name of a medical procedure performed Medical Facility 1, and maps, translates, and/or renames it to the code and/or name of the corresponding medical procedure performed Medical Facility 3, which in this example is "Abd/Pelvis CT" 1014. In the foregoing example, a one-to-one mapping is used, wherein medical procedure codes and/or names at one medical facility map directly to medical procedure codes and/or names at another medical facility.

Referring to FIG. 10, alternatively, the medical procedure mapping module located at the source medical facility, in this example, Medical Facility 1 1004, can be configured to use the medical procedure mapping module to map, translate, and/or rename the medical procedures to the corresponding codes and/or names in a standardized mapping table and/or standardized intermediary code system stored at the main server system 1018. The standardized mapping table and/or standardized intermediary code system can be accessed in the main server 1018 in real-time or a copy of the standardized mapping table and/or standardized intermediary code system can be transferred, distributed, or pushed out periodically to the client server systems so that the information can be accessed locally and without accessing the main server 1018. The mapped, translated, and/or renamed the medical procedure having the standardized nomenclature can be transferred to the destination medical facility, for example, Medical Facility 2 or 3. The client server system at the destination medical facility medical, for example, Medical Facility 2 or 3, can use the procedure mapping module and the standardized mapping table to map, translate, and/or rename the medical procedure having the standardized nomenclature to the codes and/or names used by the destination medical facility. In the foregoing example, medical procedure codes and/or names at one medical facility are mapped first to a standardized mapping schema or table, and then the standardized mapping codes and/or names are mapped to the multiple medical procedure codes and/or names at other medical facilities Referring to FIG. 10, the medical procedure mapping module can also be configured to allow a medical professional, with the appropriate authorization and/or system privileges, to manually review, analyze, approve, override, set, and/or identify the code and/or name of the medical procedure to be associated with the medical file. The setting chosen by the medical professional can be temporary (for example, a special code or name for the medical file) or can be stored for similar medical files received in the future. As such, the medical procedure mapping module can be configured to remember and/or save the setting manually performed or selected by the medical professional so that similar medical files received in the future will automatically be associated with the code and/or name of the medical procedure. Accordingly, the medical procedure mapping module can learn over time the proper codes and/or names to be associated with certain medical files, or build a mapping table over time. Alternatively, the medical procedure mapping module can be configured with a mapping table during the initial setup or during periodic updating of the client server system and/or the main server system.

In some embodiments, the acts, methods, and processes described herein are implemented within, or using, software modules (programs) that are executed by one or more general purpose computers. The software modules may be stored on or within any suitable computer-readable medium. It should be understood that the various steps may alternatively be implemented in-whole or in-part within specially designed hardware. The skilled artisan will recognize that not all calculations, analyses and/or optimization require the use of computers, though any of the above-described methods, calculations or analyses can be facilitated through the use of computers.

Marking Medical Files/Examinations "Signed"

Figure 11:
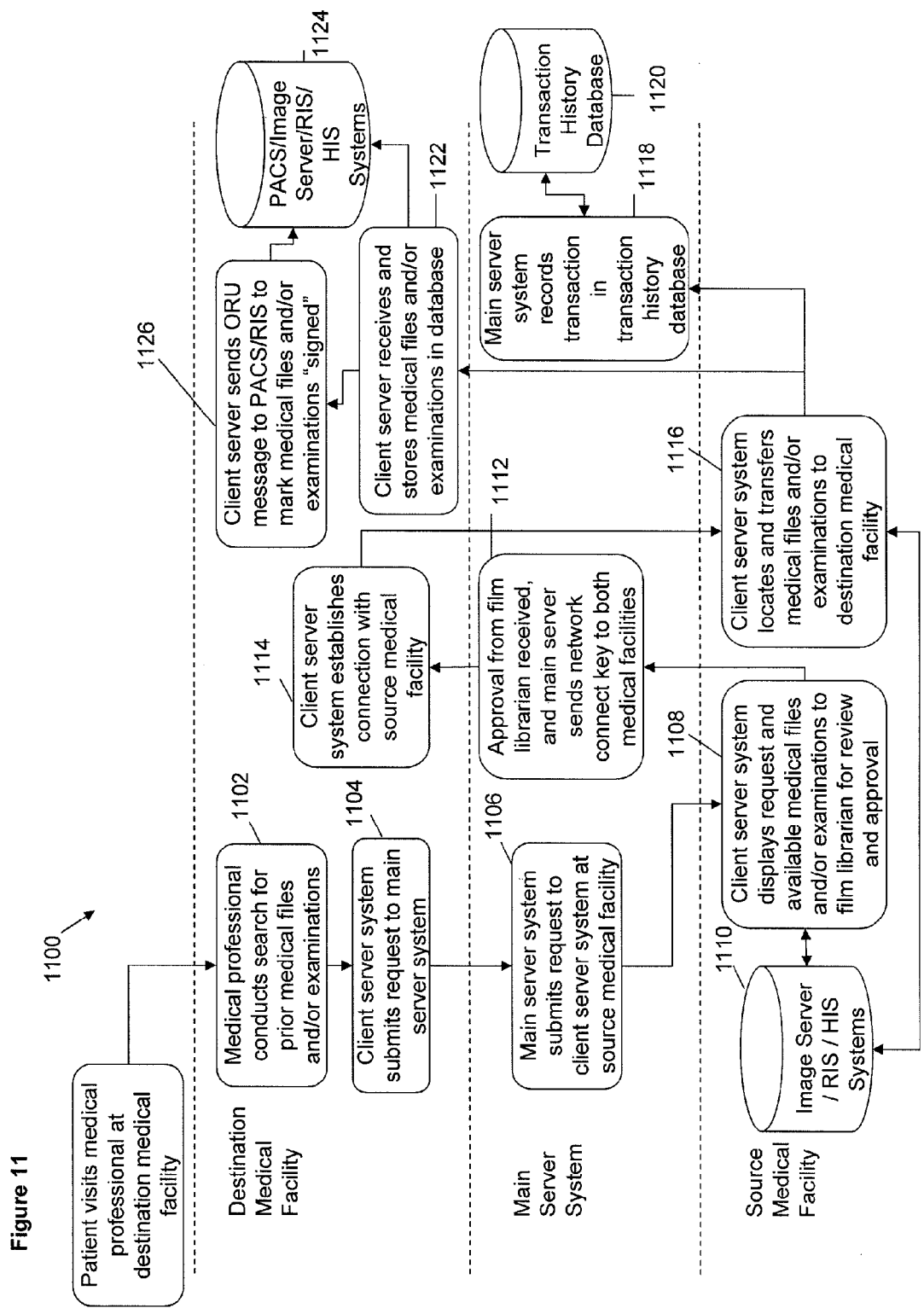
FIG. 11. depicts an example of one embodiment of a process flow diagram illustrating an example of transferring and/or marking a transferred medical file.
Figure 7:
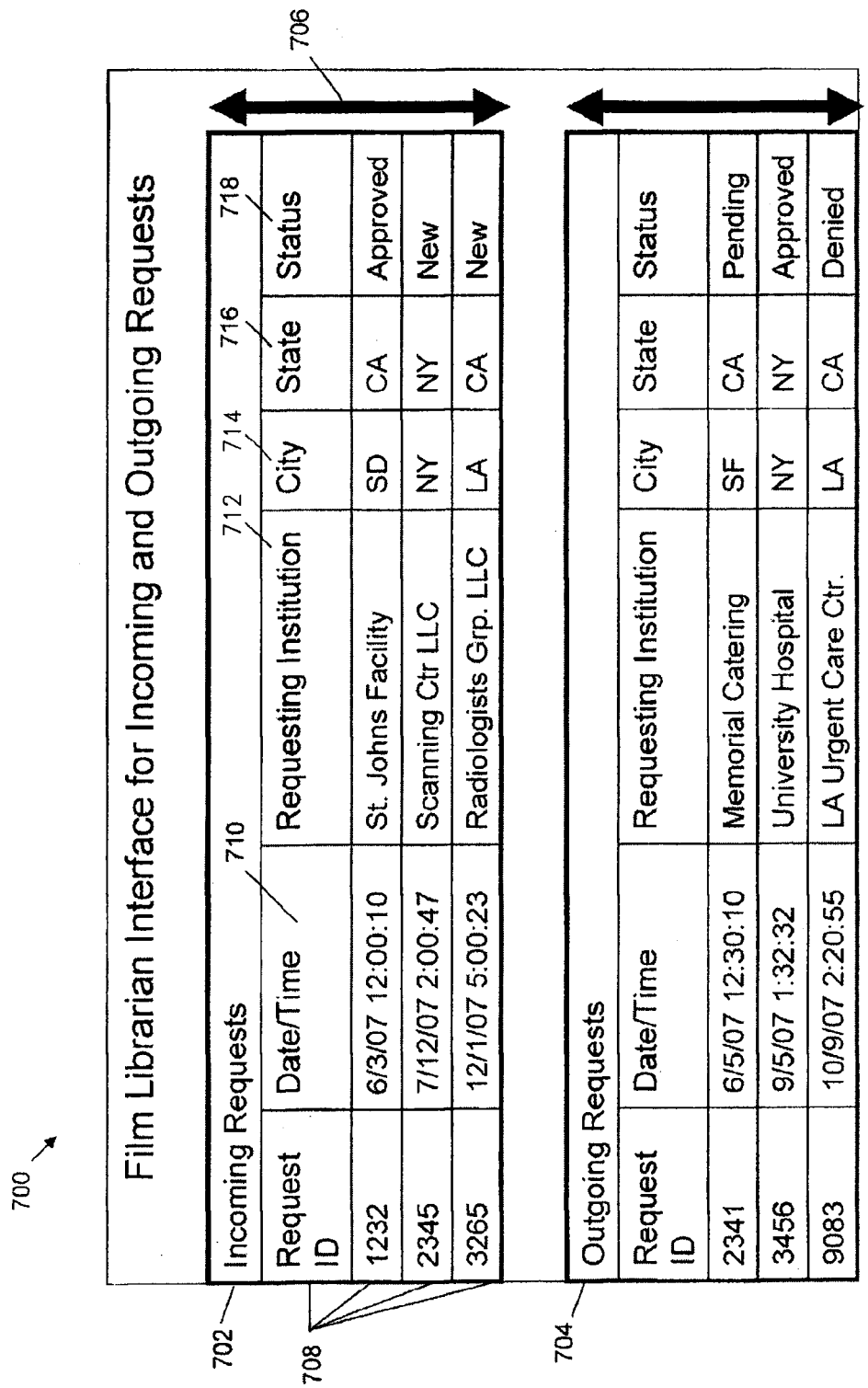

With reference to FIG. 11, when importing medical files and/or examinations from a source medical facility to a destination medical facility, the transferred medical files and/or examinations are generally listed in a work list as a new medical file and/or examination for a medical professional to review, analyze, and process; however, such transferred medical files and/or examinations have generally been reviewed and analyzed by a medical professional at the source medical facility. To review and analyze a new medical file and/or examination, it is processed over several stages, for example, approved, unread, read, preliminary interpretation, and/or final interpretation/signed steps. To ensure that already reviewed and analyzed medical files and/or reports do not go through the foregoing processing stages, the client server system can be configured to use an Observation Result (ORU) message, and/or equivalent message, system communications, or the like, to properly mark the medical files and/or examinations as "signed" or electronically signed (process 1100).

Referring to FIG. 11, in the HL7 Standard, an ORU is usually in response to an order and provides clinical observations. In HL7 messaging, ORU messages provide structured patient-oriented clinical data between systems (for example, EKG results to a physician's office). ORU messages also can be used for linking orders and results to clinical trials (for example, new drugs or new devices). Clinical observations can include without limitation: clinical laboratory results, imaging studies (for example, text), EKG pulmonary function studies, and/or interpretations, and/or the like.

Regarding FIG. 11, in certain embodiments, the client server system can be configured to use an ORU message, and/or equivalent message, system communication, or the like, to set a flag or status flag in a PACS, RIS, HIS, and/or other system, or to trigger a PACS, RIS, HIS, and/or other system to mark selected medical files and/or examinations as "signed" (block 1126). For example, after a client server system at a destination medical facility receives medical files and/or examinations from a source medical facility, the client server system can be configured to store the medical files and/or examinations into the medical facility's PACS, HIS, RIS, and/or image server systems using a direct HL7 and/or DICOM connection at block 1122. In certain embodiments, the client server system is configured to use an ORU, and/or equivalent message, system communication, or the like, to set a flag or status flag in the RIS, HIS, and/or PACS, or to trigger the RIS, HIS, and/or PACS at block 1126 to mark the recently stored medical files and/or examinations as "signed" or approved, reviewed, and/or analyzed so that the medical files, and/or examinations do not appear to a medical professional as unread and/or a new study. Marking the medical files and/or examinations as "signed" generally prevents the medical professional from reviewing already reviewed medical files and/or examinations, and allows the medical professional to use the medical files and/or examinations for historical review or comparison purposes.

Report Forwarding

In certain embodiments, the source medical facility is an emergency room, hospital, clinic, doctor's office, or the like, and the destination medical facility is a third party that provides outsourced radiology film interpretation/analysis and/or other medical services. For example, such third parties include without limitation NightHawk Radiology Services®, Virtual Radiologic, Quality Nighthawk, US Radiology On-Call, or the like. These third parties are generally employed by the source medical facility to read, analyze, and/or interpret the medical files and/or examinations generated at the source medical facility, and to transfer back such analysis, consultation, reports, images, or the like to the source medical facility for the medical professionals to review, analyze, and relay to the patient.

In this example, the medical files and/or examinations may need to be transferred or forwarded from the source medical facility to the destination medical facility wherein the transferred medical files and/or examinations are marked new, unread, unanalyzed, and/or unsigned at the destination medical facility. The client server system, in certain embodiments, is configured to automatically forward medical files and/or examinations to a destination medical facility based on a criterion, for example, a specific time period (low staffing period), periodic basis, in real time, or other basis. The criterion can also include but is not limited to being based on a specific time period (for example off-hours), based on staffing available (for example, scheduled staffing or real time assessment of staffing and/or current work load) at the medical facility, based on a specific examination type or specialty required, or any other criteria. Alternatively, the client server system can be configured to forward a file copy of or an electronic copy of all or substantially all images, medical files, and/or examinations received on a specific TCP/IP port to a destination medical facility. The medical files and/or examinations are marked new, unread, unanalyzed, and/or unsigned so that the third party medical professionals will be notified to review, analyze, and interpret the transferred medical files and/or examinations.

Generally, when transferring medical files and/or examinations, the destination medical facility may automatically import and/or display the medical files and/or examinations in a work list or the like, and mark the medical files and/or examinations as new, unread, unanalyzed, and/or unsigned. In certain embodiments, the client server system at a destination medical facility is configured to store the medical files and/or examinations into the medical facility's PACS, HIS, RIS, and/or image server systems using a direct DICOM and/or HL7 and/or other connections. The client server system can also be configured to use an ORU, and/or equivalent message, system communication, or the like, to set a flag or status flag in the PACS, RIS, HIS and/or other systems, or to trigger the PACS, RIS, HIS, and/or other system to mark the recently stored medical files and/or examinations as "unsigned" or unapproved, not reviewed, and/or unanalyzed so that a medical professional will be notified to review, analyze, and/or interpret the recently transferred and/or stored medical files, and/or examinations.

After reviewing, analyzing, interpreting, and/or signing the medical files and/or examinations, the client server can be configured to transfer the signed medical files, medical reports and/or examinations back to the source medical facility and/or other medical facilities. In transferring the signed medical reports and/or examinations back, the client server system at the source medical facility and/or at other medical facilities can be configured to use an ORU message, and/or equivalent message, system communication, or the like, to set a flag or status flag in a PACS and/or RIS, or to trigger a PACS and/or RIS to mark the medical files and/or examinations as "signed" if so desired.

Enterprise Master Patient Index

Enterprise Master Patient Index or Enterprise-wide Master Patient Index (EMPI), are Master Patient Indexes (MPI) or Patient Master Indexes (PMI), which link several smaller organization level MPIs together. In medical systems, a MPI is an index referencing all or substantially all patients known to an area, enterprise or organization. In certain embodiments, the client server systems and/or the main server systems are configured to connect and communicate with EMPI, MPI, and/or PMI systems to locate, search, retrieve, and store medical files, examinations, and/or other data.

Medical File Back-Up Module

In certain embodiments, medical facilities may require that medical files and other data be stored and/or backed-up at an off-site facility and/or at a third party service provider. Such requirements may be due to government regulations, disaster preparedness planning, cost/maintenance policies, and/or other medical facility policies. In certain embodiments, the client server system is configured to automatically forward medical files and/or examinations to a medical facility, third party service provider, off-site facility or the like that acts as a backup storage facility.

File and/or Message Conversion Module

In certain embodiments, the medical facilities may require that medical files and/or other data files that are transferred into and/or out of the medical facility be converted into a different file format and/or type so that the medical files, medical system messages, and/or other data files are compatible with and/or may be read by the systems and/or computer systems at the medical facility. In certain embodiments, the file and/or message conversion module can be configured to convert medical files, medical system messages, and/or other data files into other types of data file formats. In certain embodiments, the medical files and/or other data files may be converted by the client server system at the source and/or destination medical facility. For example, the medical files and/or other data files may be converted from a Microsoft® Word file to a WordPerfect® file, and/or the like. Other example file conversions include without limitation DICOM using JPEG2000 to DICOM using JPEG, DICOM to JPEG, Microsoft® Word to ASCII text, and the like. In certain embodiments, the file and/or message conversion module can be configured to convert, transform, and/or reformat system messages, for example, HL7 messages, into other message formats and/or types to be compatible with other hospital systems, for example, RIS, HIS, PACS, and/or other formats. This converting, transformation and/or reformatting process can be specific down to the individual character.

In certain embodiments, the file and/or message conversion module can be configured to determine the file format type by reviewing the extension name of the file and/or analyzing the contents of the files. The file and/or message conversion module can be configured to convert multiple medical files and/or other data files as an entire set.

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above.

What is claimed is:

1. A computer-implemented method of electronically transferring medical files from a source medical facility to a destination medical facility, the method comprising:
   receiving by a computer system over a computer network an authorization message from a user access point system, the authorization message configured to permit electronic transmission of a first electronic medical file from a source computing system of the source medical facility to a destination computing system of the destination medical facility;
   obtaining access by the computer system to the first electronic medical file stored in the source computing system, the first electronic medical file including a first patient identifier;
   modifying or causing modification of by the computer system the first electronic medical file by removing the first patient identifier and replacing the first patient identifier in the first electronic medical file with a second patient identifier or otherwise associating the first electronic medical file with the second patient identifier, wherein the source computing system uses the first patient identifier for identifying a patient, and the destination computing system uses the second patient identifier for identifying the patient; and
   transmitting electronically or causing the electronic transmission of the first electronic medical file from a data store to a computing device of the destination computing system over the computer network,
   wherein the computer system comprises a computer processor and an electronic storage medium.

2. The computer-implemented method of claim 1, wherein the user access point system is configured to be operated by the patient or a representative of the patient.

3. The computer-implemented method of claim 1, wherein the computer system comprises one or more computer systems.

4. The computer-implemented method of claim 1, wherein the computer system is accessible by the source computing system.

5. The computer-implemented method of claim 1, wherein the computer system is accessible by the destination computing system.

6. The computer-implemented method of claim 1, wherein a main server computing system comprises the computer system, and wherein the main server computing system is configured to control the electronic transmission of the first electronic medical file by processing a request to electronically transmit the first electronic medical file from the source computing system to the destination computing system and by initiating the electronic transmission thereof.

7. The computer-implemented method of claim 1, further comprising storing the first patient identifier and the second patient identifier in an electronic data repository, wherein the electronic data repository is configured to store a plurality of patient identifiers associated with the patient at a plurality of medical facilities.

8. The computer-implemented method of claim 1, wherein electronic medical files in the source computing system are incompatible with the destination computing system, and wherein the computer-implemented method further comprises modifying by the computer system an electronic file format of the first electronic medical file to make the first electronic medical file compatible with the destination computing system.

9. The computer-implemented method of claim 1, wherein the user access point system is a mobile device comprising an interface module configured to display output data and to receive input data for transmission over the computer network to the computer system.

10. The computer-implemented method of claim 1, wherein the user access point system is a desktop computer comprising an interface module configured to display output data and to receive input data for transmission over the computer network to the computer system.

11. A computer-readable, non-transitory storage medium having a computer program stored thereon for causing a suitably programmed computer system to process by one or more computer processors computer-program code by performing a method when the computer program is executed on the suitably programmed computer system, the method comprising:
   receiving by the computer system over a computer network an authorization message from a user access point system, the authorization message configured to permit electronic transmission of a first electronic medical file from a source computing system to a destination computing system;
   obtaining access by the computer system to the first electronic medical file stored in the source computing system, the first electronic medical file including a first patient identifier;
   modifying or causing modification of by the computer system the first electronic medical file by removing the first patient identifier and replacing the first patient identifier in the first electronic medical file with a second patient identifier or otherwise associating the first electronic medical file with the second patient identifier, wherein the source computing system uses the first patient identifier for identifying a patient, and the destination computing system uses the second patient identifier for identifying the patient; and
   transmitting electronically or causing the electronic transmission of the first electronic medical file from a data store to a computing device of the destination computing system over the computer network,
   wherein the computer system comprises a computer processor and an electronic storage medium.

12. The computer-readable, non-transitory storage medium of claim 11, wherein the user access point system is configured to be operated by the patient or a representative of the patient.

13. The computer-readable, non-transitory storage medium of claim 11, wherein the computer system comprises one or more computer systems.

14. The computer-readable, non-transitory storage medium of claim 11, wherein the computer system is accessible by the source computing system.

15. The computer-readable, non-transitory storage medium of claim 11, wherein the computer system is accessible by the destination computing system.

16. The computer-readable, non-transitory storage medium of claim 11, wherein a main server computing system comprises the computer system, and wherein the main server computing system is configured to control the electronic transmission of the first electronic medical file by processing a request to electronically transmit the first electronic medical file from the source computing system to the destination computing system and by initiating the electronic transmission thereof.

17. The computer-readable, non-transitory storage medium of claim 11, wherein the method further comprises storing the first patient identifier and the second patient identifier in an electronic data repository, wherein the electronic data repository is configured to store a plurality of patient identifiers associated with the patient at a plurality of medical facilities.

18. The computer-readable, non-transitory storage medium of claim 11, wherein electronic medical files in the source computing system are incompatible with the destination computing system, and wherein the method further comprises modifying by the computer system an electronic file format of the first electronic medical file to make the first electronic medical file compatible with the destination computing system.

19. The computer-readable, non-transitory storage medium of claim 11, wherein the user access point system is a mobile device comprising an interface module configured to display output data and to receive input data for transmission over the computer network to the computer system.

20. The computer-readable, non-transitory storage medium of claim 11, wherein the user access point system is a desktop computer comprising an interface module configured to display output data and to receive input data for transmission over the computer network to the computer system.

21. A computer system for electronically transferring medical files from a source medical facility to a destination medical facility, the computer system comprising:
an electronic memo storage configured to store modules; and
a computer processor configured to execute the modules comprising at least:
an authorization module programmed to receive over a computer network an authorization message from a user access point system, the authorization message configured to permit electronic transmission of a first electronic medical file from a source computing system to a destination computing system;
an access module programmed to obtain access to the first electronic medical file stored in the source computing system, the first electronic medical file including a first patient identifier;
a modification module programmed to modify or cause modification of the first electronic medical file by removing the first patient identifier and replacing the first patient identifier in the first electronic medical file with a second patient identifier or otherwise associating the first electronic medical file with the second patient identifier, wherein the source computing system uses the first patient identifier for identifying a patient, and the destination computing system uses the second patient identifier for identifying the patient; and
a transfer module programmed to transmit electronically or cause the electronic transmission of the first electronic medical file from the source computing system to a computing device of the destination computing system over the computer network.

22. The computer system of claim 21, wherein the user access point system is configured to be operated by the patient or a representative of the patient.

23. The computer system of claim 21, wherein the storage computer system is accessible by the source computing system.

24. The computer system of claim 21, wherein the storage computer system is accessible by the destination computing system.

25. The computer system of claim 21, wherein a main server computing system comprises the storage computer system, and wherein the main server computing system is configured to control the electronic transmission of the first electronic medical file by processing a request to electronically transmit the first electronic medical file from the source computing system to the destination computing system and by initiating the electronic transmission thereof.

26. The computer system of claim 21, wherein the source computing system uses a different patient identification system than the destination computing system.

27. The computer system of claim 21, further comprising an electronic data repository configured to store the first patient identifier and the second patient identifier, wherein the electronic data repository is further configured to store a plurality of patient identifiers associated with the patient at a plurality of medical facilities.

28. The computer system of claim 21, wherein electronic medical files in the source computing system are incompatible with the destination computing system, and wherein the computer processor is further configured to execute a conversion module programmed to modify an electronic file format of the first electronic medical file to make the first electronic medical file compatible with the destination computing system.

29. The computer system of claim 21, wherein the user access point system is a mobile device comprising an interface module configured to display output data and to receive input data for transmission over the computer network to the computer system.

30. The computer system of claim 21, wherein the user access point system is a desktop computer comprising an interface module configured to display output data and to receive input data for transmission over the computer network to the computer system.

* * * * *

UNITED STATES PATENT AND TRADEMARK OFFICE
CERTIFICATE OF CORRECTION

| | | |
|---|---|---|
| PATENT NO. | : 8,386,278 B2 | Page 1 of 2 |
| APPLICATION NO. | : 13/443792 | |
| DATED | : February 26, 2013 | |
| INVENTOR(S) | : Maresh et al. | |

It is certified that error appears in the above-identified patent and that said Letters Patent is hereby corrected as shown below:

In the Drawings:

In sheet 8 of 13, figure 7, remove sheet 8 and insert the corrected drawing page attached.

In the Specifications:

In column 11 at line 63, Change "MS" to --RIS--.

In column 11 at line 64, Change "MS" to --RIS--.

In column 12 at line 15, After "that" delete "that".

In column 17 at line 53, Change "an/or" to --and/or--.

In column 23 at line 64, Change "system." to --system--.

In column 27 at line 5, Change "MS" to --RIS--.

In column 27 at line 17, Change "identify" to --identity--.

In column 33 at line 54, Change "facilities" to --facilities.--.

In the Claims:

In column 39 at line 48, In Claim 21, change "memo" to --memory--.

Signed and Sealed this
Twenty-seventh Day of August, 2013

Teresa Stanek Rea
*Acting Director of the United States Patent and Trademark Office*